United States Patent
Clark et al.

(10) Patent No.: US 7,569,602 B2
(45) Date of Patent: Aug. 4, 2009

(54) FURAN DERIVATIVES AS $EP_4$ RECEPTOR ANTAGONISTS

(75) Inventors: David Edward Clark, Harlow (GB); Neil Victor Harris, Harlow (GB); Garry Fenton, Harlow (GB); George Hynd, Harlow (GB); Keith Alfred James Stuttle, Harlow (GB); Jonathan Mark Sutton, Harlow (GB); Alexander William Oxford, Royston (GB); Richard Jon Davis, Royston (GB); Robert Alexander Coleman, Royston (GB); Kenneth Lyle Clark, Royston (GB)

(73) Assignee: Asterand UK Limited, Royston Hertfordshire (GB)

( * ) Notice: Subject to any disclaimer, the term of this patent is extended or adjusted under 35 U.S.C. 154(b) by 462 days.

(21) Appl. No.: 10/576,095

(22) PCT Filed: Oct. 15, 2004

(86) PCT No.: PCT/GB2004/004392

§ 371 (c)(1),
(2), (4) Date: Apr. 14, 2006

(87) PCT Pub. No.: WO2005/037812

PCT Pub. Date: Apr. 28, 2005

(65) Prior Publication Data

US 2007/0135503 A1    Jun. 14, 2007

Related U.S. Application Data

(60) Provisional application No. 60/512,200, filed on Oct. 20, 2003.

(30) Foreign Application Priority Data

Oct. 16, 2003   (GB)   ................... 0324269.0

(51) Int. Cl.
*A61K 31/341*   (2006.01)
*C07D 307/34*   (2006.01)

(52) U.S. Cl. ................. 514/461; 549/200; 549/429; 549/483; 549/487

(58) Field of Classification Search ............. 549/200, 549/429, 483, 487; 514/461
See application file for complete search history.

(56) References Cited

U.S. PATENT DOCUMENTS 5,602,136 A   2/1997   Ruhter et al.

(Continued)

FOREIGN PATENT DOCUMENTS

EP   661260   7/1995

(Continued)

OTHER PUBLICATIONS

International Search Report of PCT/GB2004/004392, mailed Jan. 31, 2005.

(Continued)

*Primary Examiner*—Golam M Shameem
(74) *Attorney, Agent, or Firm*—Nixon & Vanderhye P.C.

(57)   ABSTRACT

A compound of formula (I):

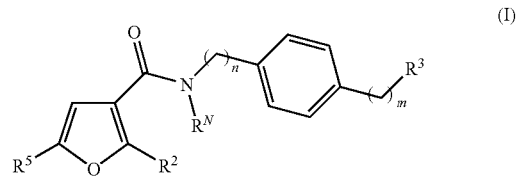

or a salt, solvate and chemically protected form thereof, wherein one of $R^2$ and $R^5$ is:

(i) H or an optionally substituted $C_{1-4}$ alkyl group; or (ii) an optionally substituted $C_{5-7}$ aryl; and the other of $R^2$ and $R^5$ is the other group;

m and n can be 0 or 1, and m+n=1 or 2

$R^N$ is H or optionally substituted $C_{1-4}$ alkyl $R^3$ is either:

(i) carboxy;

(ii) a group of formula (II):

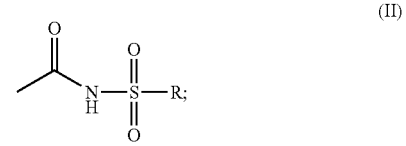

(iii) a group of formula (III):

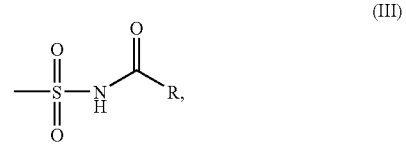

wherein R is optionally substituted $C_{1-7}$ alkyl, $C_{5-20}$ aryl, or $NR^{N3}R^{N4}$, where $R^{N3}$ and $R^{N4}$ are independently selected from optionally substituted $C_{1-4}$ alkyl; or (iv) tetrazol-5-yl.

13 Claims, No Drawings

U.S. PATENT DOCUMENTS

| | | | |
|---|---|---|---|
| 5,607,951 A | 3/1997 | Macor et al. |
| 5,645,566 A | 7/1997 | Brenneman et al. |
| 5,663,357 A | 9/1997 | Teng et al. |
| 5,679,692 A | 10/1997 | Friary et al. |
| 5,686,445 A | 11/1997 | Albright et al. |
| 5,834,468 A | 11/1998 | Breault et al. |
| 5,883,106 A | 3/1999 | Stevens et al. |
| 5,939,436 A | 8/1999 | Carling et al. |
| 5,977,170 A | 11/1999 | Commons et al. |
| 6,008,362 A | 12/1999 | Commons et al. |
| 6,121,671 A | 9/2000 | Ko et al. |
| 6,162,819 A | 12/2000 | Schindler et al. |
| 6,184,245 B1 | 2/2001 | Sugawara et al. |
| 6,211,197 B1 | 4/2001 | Belley |
| 6,291,677 B1 | 9/2001 | Vasudevan et al. |
| 6,380,218 B1 | 4/2002 | Moarfat et al. |
| 6,610,719 B2 | 8/2003 | Paralkar et al. |
| 6,716,864 B2 | 4/2004 | Burk et al. |
| 6,765,004 B1 | 7/2004 | Hoekstra |
| 6,797,712 B2 | 9/2004 | Maul et al. |
| 6,835,212 B2 | 12/2004 | Rozzell et al. |
| 6,849,641 B1 | 2/2005 | Tang et al. |
| 6,855,706 B2 | 2/2005 | Tanaka et al. |
| 6,861,441 B1 | 3/2005 | Clayton et al. |
| 6,878,740 B2 | 4/2005 | Sundermann et al. |
| 6,956,057 B2 | 10/2005 | Woodward et al. |
| 7,196,089 B2 | 3/2007 | Oxford |
| 7,417,068 B2 | 8/2008 | Clark |
| 2002/0040024 A1 | 4/2002 | Apodaca et al. |
| 2002/0115671 A1 | 8/2002 | Goehring et al. |
| 2002/0137736 A1 | 9/2002 | Mattes et al. |
| 2003/0100583 A1 | 5/2003 | Bernardon |
| 2003/0119817 A1 | 6/2003 | Mehta et al. |
| 2003/0195190 A1 | 10/2003 | Peschke et al. |
| 2004/0048889 A1 | 3/2004 | Peters et al. |
| 2004/0147559 A1 | 7/2004 | Taveras et al. |
| 2004/0152734 A1 | 8/2004 | Sundermann et al. |
| 2004/0192758 A1 | 9/2004 | Leban et al. |
| 2004/0192767 A1 | 9/2004 | Oxford et al. |
| 2004/0235888 A1 | 11/2004 | Yamamori et al. |
| 2004/0259880 A1 | 12/2004 | Lockhart et al. |
| 2005/0004133 A1 | 1/2005 | Makings et al. |
| 2005/0043386 A1 | 2/2005 | Nishi et al. |
| 2005/0176987 A1 | 8/2005 | Goossen et al. |

FOREIGN PATENT DOCUMENTS

| | | |
|---|---|---|
| EP | 776885 | 6/1997 |
| EP | 1108426 | 6/2001 |
| EP | 1 258 473 | 11/2002 |
| EP | 1 258 473 A1 | 11/2002 |
| JP | 03-240066 | 10/1991 |
| JP | 04-253974 | 9/1992 |
| JP | 07-281440 | 10/1995 |
| JP | 09-311401 | 12/1997 |
| JP | 10-287654 | 10/1998 |
| JP | 11-209366 | 1/1999 |
| JP | 2001-139550 | 5/2001 |
| JP | 2004-051628 | 2/2004 |
| JP | 2005-41867 | 2/2005 |
| JP | 2005-046141 | 2/2005 |
| WO | WO9117163 | 11/1991 |
| WO | WO9118897 | 12/1991 |
| WO | WO9221644 | 12/1992 |
| WO | WO9303012 | 2/1993 |
| WO | WO9306118 | 4/1993 |
| WO | WO9402460 | 2/1994 |
| WO | WO9402483 | 2/1994 |
| WO | WO9406796 | 3/1994 |
| WO | WO9521171 | 8/1995 |
| WO | WO9601827 | 1/1996 |
| WO | WO9611911 | 4/1996 |
| WO | WO9807835 | 2/1998 |
| WO | WO9834909 | 8/1998 |
| WO | WO9847894 | 10/1998 |
| WO | WO9851662 | 11/1998 |
| WO | WO9856783 | 12/1998 |
| WO | WO9857925 | 12/1998 |
| WO | WO9857927 | 12/1998 |
| WO | WO9857928 | 12/1998 |
| WO | WO9910322 | 3/1999 |
| WO | WO9919300 | 4/1999 |
| WO | WO/00/06529 | 2/2000 |
| WO | WO 00/18405 | 4/2000 |
| WO | WO/00/18405 | 4/2000 |
| WO | WO/00/24738 | 5/2000 |
| WO | WO/0040561 | 7/2000 |
| WO | WO/0069987 | 11/2000 |
| WO | WO/0157006 | 8/2001 |
| WO | WO/0164676 | 9/2001 |
| WO | WO 01/72302 | 10/2001 |
| WO | WO/0206278 | 1/2002 |
| WO | WO02/18361 | 3/2002 |
| WO | WO02/26727 | 4/2002 |
| WO | WO02/40473 | 4/2002 |
| WO | WO/02058698 | 8/2002 |
| WO | WO/02060898 | 8/2002 |
| WO | WO/02067930 | 9/2002 |
| WO | WO/02067937 | 9/2002 |
| WO | WO02068412 | 9/2002 |
| WO | WO02/083624 | 10/2002 |
| WO | WO03/018585 | 3/2003 |
| WO | WO0/3033503 | 4/2003 |
| WO | WO0/3044015 | 5/2003 |
| WO | WO03/053352 | 7/2003 |
| WO | WO03/055479 | 7/2003 |
| WO | WO03/059871 | 7/2003 |
| WO | WO03/097621 | 11/2003 |
| WO | WO03/097644 | 11/2003 |
| WO | WO03090869 | 11/2003 |
| WO | WO2004/002948 | 1/2004 |
| WO | WO2004/011418 | 2/2004 |
| WO | WO2004/019932 | 3/2004 |
| WO | WO2004/024663 | 3/2004 |
| WO | WO2004024738 | 3/2004 |
| WO | WO2004048349 | 6/2004 |
| WO | WO2004063194 | 7/2004 |
| WO | WO2004069816 | 8/2004 |
| WO | WO2004078169 | 9/2004 |
| WO | WO2004089944 | 10/2004 |
| WO | WO2004094362 | 11/2004 |
| WO | WO2004099199 | 11/2004 |
| WO | WO2005079793 | 9/2005 |

OTHER PUBLICATIONS

Lapina et al (2001): STN International HCAPLUS database, Columbus (OH), accession No. 2002: 200984.

Berge et al, Journal of Pharmaceutical Sciences, Jan. 1977, vol. 66, No. 1, pp. 1-19.

Lapina et al,,Russian Journal of General Chemistry, 2001, vol. 71, No. 9, pp. 1479-1483.

Hoekstra et al (2000): STN International HCAPLUS database, Columbus (OH), accession No. 2000: 91 1255.

Richard J Davis et al. $EP_4$ prostanoid receptor-mediated vasodilatation of human middle cerebral arteries. Br. J. Pharmacol. (2004) 141, 580-585.

Berge, et al., "Pharmaceutically Acceptable Salts", J. Pharm. Sci., 1977, vol. 66, pp. 1-19.

Arunlakshana, O., et al., "Some quantitative use of drug antagonists", Brit. J. Pharmacol., 1959, vol. 14, pp. 48-58.

Porretta, G. C., et al., "Research on antibacterial and antifungal agents", II Farmaco, Ed. Sc., 1987, vol. 42, No. 9, pp. 629-639.

Modrakowski, C., et al., "Synthesis of Pyrene Containing Building Blocks for Dendrimer Synthesis", Synthesis, 2001, No. 14, pp. 2143-2155.

Wenkert, E., et al., "Polyene Synthesis. Ready Construction of Retinol-Carotene Fragments, (±)-6(E)-LTB3 Leukotrienes, and Corticrocin", J. Org. Chem., 1990, vol. 55, No. 25, pp. 6203-6214.

Bures, E., "Regioselective Preparation of 2,4-, 3,4,- and 2,3,4-Substituted Furan Rings.", J. Org. Chem., 1997, vol. 62, No. 25, pp. 8741-8749.

Wang, Y., et al., "A simple synthesis of fluoroalkyl substituted dihydrofurans by rhodium(II)-catalysed 1,3-dipolar reactions", Tetrahedron, 2001, vol. 57, No. 16, pp. 3383-3387.

Bin, Y., "A Concise Synthesis of the Differentiating Antibiotic L-Azatyrosine", J. Org. Chem., 1995, vol. 60, No. 8, pp. 2640-2641.

Doll, M. H., et al., "Irreversible Enzyme Inhibitors. Inhibitors of Guinea Pig Complement Derived by Quaternization of Substituted Pyridines with Benzyl Halides", J. Med. Chem., 1976, vol. 19, No. 9, pp. 1079-1088.

Mndzhoyan, A. L., et al., Doklady Akademii Nauk Armyanskoi SSR, 1957, vol. 25, pp. 277-280.

Valenta, M., et al., "Experiments in the furan series. III. Preparation of some 2,3,5-trisubstituted derivatives", Collection Czechoslov. Chem. Commun., 1964, vol. 29, pp. 1577-1581.

FURAN DERIVATIVES AS EP$_4$ RECEPTOR ANTAGONISTS

This application is the US national phase of international application PCT/GB2004/004392, filed 15 Oct. 2004, which designated the U.S. and claims priority of GB 0324269.0, filed 16 Oct. 2003, and U.S. 60/512,200, filed 20 Oct. 2003, the entire contents of each of which are hereby incorporated by reference.

This invention relates to EP$_4$ receptor antagonists, pharmaceutical compositions comprising such compounds, and the use of such compounds and compositions to treat various diseases.

BACKGROUND TO THE INVENTION

Prostanoids comprise prostaglandins (PGs) and thromboxanes (Txs) and their receptors fall into five different classes (DP, EP, FP, IP and TP) based on their sensitivity to the five naturally occurring prostanoids, PGD$_2$, PGE$_2$, PGF$_{2\alpha}$, PGI$_2$ and TxA$_2$, respectively (Coleman, R. A., Prostanoid Receptors. *IUPHAR compendium of receptor characterisation and classification*, 2$^{nd}$ edition, 338-353, ISBN 0-9533510-3-3, 2000). EP receptors (for which the endogenous ligand is PGE$_2$) have been subdivided into four types termed EP$_1$, EP$_2$, EP$_3$ and EP$_4$. These four types of EP receptors have been cloned and are distinct at both a molecular and pharmacological level (Coleman, R. A., 2000)

EP$_4$ antagonists have been shown to be useful in the treatment of pain, and in particular, in the treatment of primary headache disorders, which include migraines, and secondary headache disorders, such as drug-induced headaches (WO 00/18405 and WO 01/72302). Dilation of the cerebral vasculature and the subsequent stimulation of pain stimulating, perivascular trigeminal sensory afferent nerves is recognised to play an important role in the pathophysiology of migraine. A sterile inflammatory response, associated with activation of cycloxygenase and the generation of PGE$_2$, is also implicated in the pathophysiology of migraine. PGE$_2$ levels have been shown to be raised during migraine attacks and PGE$_2$ contributes to the pain of migraine by directly dilating cerebral arteries and by stimulating the release of vasoactive/pro-inflammatory peptides from the trigeminal nerves. These effects of PGE$_2$ are mediated in whole or in part by EP$_4$ receptors. Thus, by binding to and preventing the stimulation of EP$_4$ receptors, EP$_4$ antagonists may be used to treat the pain of migraine.

EP$_4$ antagonists may also be useful in treating a number of other conditions and diseases. For example, they may be used in:

the treatment of pain associated with rheumatoid arthritis, osteoarthritis, rheumatoid spondylitis, gouty arthritis and juvenile arthritis;

the treatment of musculoskeletal pain, lower back and neck pain, sprains and strains, neuropathic pain, sympathetically mediated pain, myositis, pain associated with cancer and fibromyalgia, pain associated with influenza or other viral infections, such as the common cold, rheumatic fever; pain associated with bowel disorders such as non-ulcer dyspepsia, irritable bowel syndrome; non-cardiac chest pain, pain associated with myocardial ischaemia, post-operative pain, headache, toothache and dysmenorrhea. Neuropathic pain syndromes include diabetic neuropathy, sciatica, non-specific lower back pain, multiple sclerosis pain, fibromyalgia, HIV-related neuropathy, post-herpetic neuralgia, trigeminal neuralgia and pain resulting from physical trauma;

the treatment of inflammatory diseases including rheumatoid and osteoarthritis, psoriasis, dermatitis, retinitis, conjunctivitis, asthma, bronchitis, chronic obstructive pulmonary disease, inflammatory bowel disease, colitis, nephritis, gingivitis and hepatitis;

the treatment of cancers including familial adenomatous polyposis, endometrial carcinoma, colorectal and cervical cancer;

the treatment of bone disorders involving altered bone formation or resorption such as osteoporosis;

women's health for the treatment of myometrial and endometrial disorders;

the treatment of gastrointestinal disease including diarrhoea;

the treatment of immunological disorders such as autoimmune disease, immunological deficiency diseases, organ transplantation and increasing the latency of HIV infection;

the treatment of diseases of abnormal platelet function. (e.g. occlusive vascular diseases);

the preparation of a drug with diuretic properties to treat or prevent various oedema, hypertension, premenstrual tension, urinary calculus, oliguria, hyperphosphaturia, mesangial proliferative glomerulonephritis, chronic renal failure or the like;

the treatment of impotence or erectile dysfunction, and female sexual dysfunction;

the treatment of hair growth disorders;

the treatment of sleep disorders such as narcolepsy and insomnia;

the treatment of cardiovascular diseases and shock states associated with hypotension (e.g. septic shock);

the treatment of neurodegenerative diseases and for preventing neuronal damage following stroke, cardiac arrest, cardiopulmonary bypass, traumatic brain injury or spinal cord injury;

the treatment of tinnitus;

the treatment of dependence; and the treatment of complications of diabetes.

Although EP$_4$ antagonists are known, it is desired to find novel EP$_4$ antagonists, and in particular, EP$_4$ antagonists which are selective against other EP receptors, i.e. EP$_1$, EP$_2$ and EP$_3$.

SUMMARY OF THE INVENTION

A first aspect of the present invention provides a compound of formula (I):

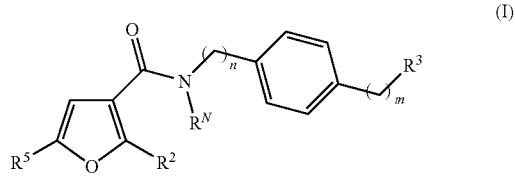

or a salt, solvate and chemically protected form thereof, wherein:

one of R$^2$ and R$^5$ is:

(i) H or an optionally substituted C$_{1-4}$ alkyl group; or (ii) an optionally substituted C$_{5-7}$ aryl; and the other of R$^2$ and R$^5$ is the other group;

m and n can be 0 or 1, and m+n=1 or 2

R$^N$ is H or optionally substituted C$_{1-4}$ alkyl

R$^3$ is either:

(i) carboxy;
(ii) a group of formula (II):

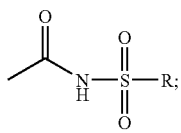

(iii) a group of formula (III):

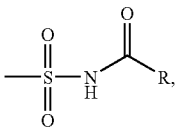

wherein R is optionally substituted $C_{1-7}$ alkyl, $C_{5-20}$ aryl, or $NR^{N3}R^{N4}$, where $R^{N3}$ and $R^{N4}$ are independently selected from optionally substituted $C_{1-4}$ alkyl; or (iv) tetrazol-5-yl.

The compound is preferably not N-(5-phenyl-2-methyl-3-furyl)-p-aminophenylacetic acid, i.e. $R^2$=$CH_3$, $R^5$=phenyl, $R^N$=H, n=0, m=1 and $R^3$=carboxy.

A second aspect of the present invention provides a compound of formula (I) or a pharmaceutically acceptable salt thereof for use in a method of therapy.

A third aspect of the present invention provides a pharmaceutical composition comprising a compound of formula (I) as defined in the first aspect or a pharmaceutically acceptable salt thereof together with a pharmaceutically acceptable carrier or diluent.

A further aspect of the present invention provides the use of a compound of formula (I) or a pharmaceutically acceptable salt thereof in the preparation of a medicament for the treatment of a condition alleviated by antagonism of an $EP_4$ receptor.

Another aspect of the present invention provides a method of treating a condition which can be alleviated by antagonism of an $EP_4$ receptor, which method comprises administering to a patient in need of treatment an effective amount of a compound of formula (I), or a pharmaceutically acceptable salt thereof.

Conditions which can be alleviated by antagonism of an $EP_4$ receptor are discussed above, and particularly include primary headache disorders, most particularly migraines.

The present invention also provides methods of antagonizing $EP_4$ receptors, in vitro or in vivo, comprising contacting a cell with an effective amount of a compound of formula (I).

In some embodiments, the compounds described above may be selective as against antagonism of the other three EP receptors, i.e. $EP_1$, $EP_2$ and $EP_3$. This selectivity allows for targeting of the effect of the compounds of the invention, with possible benefits in the treatment of certain conditions.

Definitions

Monodentate Groups (i.e. Groups with One Point of Covalent Attachment)

Alkyl: The term "alkyl" as used herein, pertains to a monovalent moiety obtained by removing a hydrogen atom from a carbon atom of a hydrocarbon compound having from 1 to 7 carbon atoms (unless otherwise specified), which may be aliphatic or alicyclic, and which may be saturated or unsaturated. Thus, the term "alkyl" includes the sub-classes alkenyl, alkynyl, cycloalkyl, cycloalkenyl, cylcoalkynyl, etc., discussed below.

In the context of alkyl groups, the prefixes (e.g. $C_{1-4}$, $C_{1-7}$) denote the number of carbon atoms, or range of number of carbon atoms. For example, the term "$C_{1-4}$ alkyl" as used herein, pertains to an alkyl group having from 1 to 4 carbon atoms. Examples of groups of alkyl groups include $C_{1-4}$ alkyl ("lower alkyl") and $C_{1-7}$ alkyl. Note that the first prefix may vary according to other limitations; for example, for unsaturated alkyl groups, the first prefix must be at least 2; for cyclic alkyl groups, the first prefix must be at least 3; etc.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Alkenyl: The term "alkenyl" as used herein, pertains to an alkyl group having one or more carbon-carbon double bonds. Examples of alkenyl groups include $C_{2-4}$alkenyl and $C_{2-7}$ alkenyl. Examples of alkenyl groups include, but are not limited to, ethenyl (vinyl, —CH═$CH_2$), 1-propenyl (—CH═CH—$CH_3$), 2-propenyl (allyl, —CH—CH═$CH_2$), isopropenyl (1-methylvinyl, —C($CH_3$)═$CH_2$), butenyl ($C_4$), pentenyl ($C_5$), and hexenyl ($C_6$).

Alkynyl: The term "alkynyl" as used herein, pertains to an alkyl group having one or more carbon-carbon triple bonds. Examples of groups of alkynyl groups include $C_{2-4}$ alkynyl and $C_{2-7}$ alkynyl. Examples of alkynyl groups include, but are not limited to, ethynyl (ethenyl, —C≡CH) and 2-propynyl (propargyl, —$CH_2$—C≡CH).

Cycloalkyl: The term "cycloalkyl" as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated, which moiety has from 3 to 7 carbon atoms (unless otherwise specified), including from 3 to 7 ring atoms. Thus, the term "cycloalkyl" includes the sub-classes cycloalkenyl and cycloalkynyl. Preferably, each ring has from 3 to 7 ring atoms. Examples of groups of cycloalkyl groups include $C_{3-7}$ cycloalkyl.

Examples of cycloalkyl groups include, but are not limited to, those derived from:
saturated monocyclic hydrocarbon compounds: cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$);
unsaturated monocyclic hydrocarbon compounds: cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$);

Heterocyclyl: The term "heterocyclyl" as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$ heterocyclyl" as used herein, pertains to a heterocyclyl group having 5 or 6 ring atoms. Examples of groups of heterocyclyl groups include $C_{3-20}$ heterocyclyl, $C_{5-20}$ heterocyclyl, $C_{3-15}$ heterocyclyl, $C_{5-15}$ heterocyclyl, $C_{3-12}$ heterocyclyl, $C_{5-12}$ heterocyclyl, $C_{3-10}$ heterocyclyl, $C_{5-10}$ heterocyclyl, $C_{3-7}$ heterocyclyl, $C_{5-7}$ heterocyclyl, and $C_{5-6}$ heterocyclyl.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Aryl: The term "aryl" as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms. Examples of groups of aryl groups include $C_{3-20}$ aryl, $C_{5-20}$ aryl, $C_{5-15}$ aryl, $C_{5-12}$ aryl, $C_{5-10}$ aryl, $C_{5-7}$ aryl, $C_{5-6}$ aryl, $C_5$ aryl, and $C_6$ aryl.

The ring atoms may be all carbon atoms, as in "carboaryl groups". Examples of carboaryl groups include $C_{3-20}$ carboaryl, $C_{5-20}$ carboaryl, $C_{5-15}$ carboaryl, $C_{5-12}$ carboaryl, $C_{5-10}$ carboaryl, $C_{5-7}$ carboaryl, $C_{5-6}$ carboaryl, $C_5$ carboaryl, and $C_6$ carboaryl.

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g., 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of heteroaryl groups include $C_{3-20}$ heteroaryl, $C_{5-20}$ heteroaryl, $C_{5-15}$ heteroaryl, $C_{5-12}$ heteroaryl, $C_{5-10}$ heteroaryl, $C_{5-7}$ heteroaryl, $C_{5-6}$ heteroaryl, $C_5$ heteroaryl, and $C_6$ heteroaryl.

Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$), pyrazine (1,4-diazine) ($C_6$);

$N_3$: triazole ($C_5$), triazine ($C_6$); and, $N_4$: tetrazole ($C_5$).

Examples of heteroaryl groups which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_3$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O$), phenothiazine ($N_1S_1$), thianthrene ($S_2$), phenanthridine ($N_1$), phenanthroline ($N_2$), phenazine ($N_2$).

If a heteroaryl or heterocyclyl group contains a nitrogen ring atom, this ring atom, where possible, may be in a oxidised state, as an N-oxide.

The above groups, whether alone or part of another substituent, may themselves optionally be substituted with one or more groups selected from themselves, the additional monodentate substituents listed below and alkoxylene.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

$C_{1-7}$ alkoxy: —OR, wherein R is a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Oxo (keto, -one): =O.

Thione (thioketone): =S.

Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of imino groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamino: —NR$^1$C(=O)R$^2$, wherein R$^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and R$^2$ is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

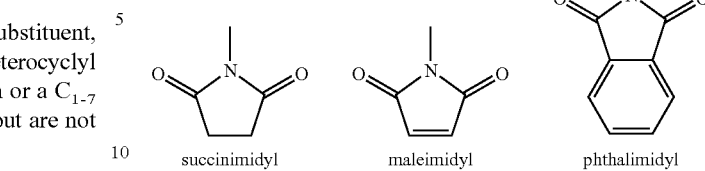

succinimidyl   maleimidyl   phthalimidyl

Thioamido (thiocarbamyl): —C(=S)NR$^1$R$^2$, wherein R$^1$ and R$^2$ are independently amino substituents, as defined for amino groups. Examples of thioamido groups include, but are not limited to, —C(=S)NH$_2$, —C(=S)NHCH$_3$, —C(=S)N(CH$_3$)$_2$, and —C(=S)NHCH$_2$CH$_3$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, R$^1$ and R$^2{}_1$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amidine (amidino): —C(=NR)NR$_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.

Nitroso: —NO.

Cyano (nitrile, carbonitrile): —CN.

Sulfhydryl (thiol, mercapto): —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —$SCH_3$ and —$SCH_2CH_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —$SSCH_3$ and —$SSCH_2CH_3$.

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O) $CH_3$ and —S(=O) $CH_2CH_3$.

Sulfone (sulfonyl): —$S(=O)_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group, including, for example, a fluorinated or perfluorinated $C_{1-7}$ alkyl group. Examples of sulfone groups include, but are not limited to, —$S(=O)_2CH_3$ (methanesulfonyl, mesyl), —$S(=O)_2CF_3$ (triflyl), —$S(=O)_2CH_2CH_3$ (esyl), —$S(=O)_2C_4F_9$ (nonaflyl), —$S(=O)_2CH_2CF_3$ (tresyl), —$S(=O)_2CH_2CH_2NH_2$ (tauryl), —$S(=O)_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —$SO_2$H.

Sulfonic acid (sulfo): —$S(=O)_2$OH, —$SO_3$H.

Sulfinate (sulfinic acid ester): —S(=O)OR; wherein R is a sulfinate substituent, for example, a $C_{1-7}$ alkyl group, a $C_{3-20}$ heterocyclyl group, or a $C_{5-20}$ aryl group, preferably a $C_{1-7}$ alkyl group. Examples of sulfinate groups include, but are not limited to, —S(=O)$OCH_3$ (methoxysulfinyl; methyl sulfinate) and —S(=O)$OCH_2CH_3$ (ethoxysulfinyl; ethyl sulfinate).

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)$CH_3$ and —OS(=O)$CH_2CH_3$.

Sulfamyl (sulfamoyl; sulfinic acid amide; sulfinamide): —$S(=O)_2NR^1R^2$, wherein $R^1$ and $R^2$ are independently amino substituents, as defined for amino groups. Examples of sulfamyl groups include, but are not limited to, —S(=O)$NH_2$, —S((=O)NH($CH_3$), —S(=O)N($CH_3$)$_2$, —S(=O)NH($CH_2CH_3$), —S((=O)N($CH_2CH_3$)$_2$, and —S(=O)NHPh.

Sulfonamido (sulfinamoyl; sulfonic acid amide; sulfonamide): —$S(=O)_2NR^1R^2$, wherein $R^1$ and $R^2$ are independently amino substituents, as defined for amino groups. Examples of sulfonamido groups include, but are not limited to, —$S(=O)_2NH_2$, —$S(=O)_2$NH($CH_3$), —$S(=O)_2$N($CH_3$)$_2$, —$S(=O)_2$NH($CH_2CH_3$), —$S(=O)_2$N($CH_2CH_3$)$_2$, and —$S(=O)_2$NHPh.

Sulfonamino: —$NR^1S(=O)_2$R, wherein $R^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —$NHS(=O)_2CH_3$ and —$N(CH_3)S(=O)_2C_6H_5$.

Sulfinamino: —$NR^1$S(=O)R, wherein $R^1$ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —NHS(=O)$CH_3$ and —N($CH_3$)S(=O)$C_6H_5$.

As already mentioned, the above described groups may be substituted, and particular examples include, but are not limited to, $C_{3-20}$ aryl-$C_{1-7}$ alkyl groups, which include benzyl (phenylmethyl, $PhCH_2$—), benzhydryl ($Ph_2$CH—), trityl (triphenylmethyl, $Ph_3$C—), phenethyl (phenylethyl, Ph-$CH_2CH_2$—), styryl (Ph-CH=CH—) and cinnamyl (Ph-CH=CH—$CH_2$—).

Bidentate Groups (i.e. Groups with Two Points of Covalent Attachment; Linking Groups)

Alkylene: The term "$C_{1-3}$ alkylene", as used herein, pertains to a bidentate moiety obtained by removing two hydrogen atoms from each of two different carbon atoms, of a linear hydrocarbon compound having from 1 to 3 carbon atoms, which may be saturated or unsaturated. Thus, the term "alkylene" includes the sub-classes alkenylene and alkynylene.

In this context, the prefix $C_{1-3}$ denotes the number of carbon atoms, or range of number of carbon atoms.

Examples of saturated $C_{1-3}$ alkylene groups include —$CH_2$— (methylene), —$CH_2CH_2$— (ethylene) and —$CH_2CH_2CH_2$— (propylene)

Examples of unsaturated $C_{1-3}$ alkylene groups (which may be termed "$C_{2-3}$ alkenylene" or "$C_{2-3}$ alkynylene", as appropriate) include —CH=CH— (vinylene), —CH=CH—$CH_2$—, —$CH_2$—CH=CH—, —C≡C—, —C≡C—$CH_2$— and —$CH_2$—C≡C—.

The $C_{1-3}$ alkylene group may be substituted by any monodentate substituent described above.

Alkoxylene: The term "alkoxylene," as used herein, pertains to a bidentate group of formula —O($CH_2$)$_n$O—, where n is 1 or 2.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO⁻), a salt or solvate thereof, as well as conventional protected forms. Similarly, a reference to an amino group includes the protonated form (—$N^+HR^1R^2$), a salt or solvate of the amino group, for example, a hydrochloride salt, as well as conventional protected forms of an amino group. Similarly, a reference to a hydroxyl group also includes the anionic form (—O⁻), a salt or solvate thereof, as well as conventional protected forms of a hydroxyl group.

Isomers, Salts, Solvates and Protected Forms

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R—, S—, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —$OCH_3$, is not to be construed as a reference to its structural isomer, a hydroxymethyl group, —CH₂OH. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

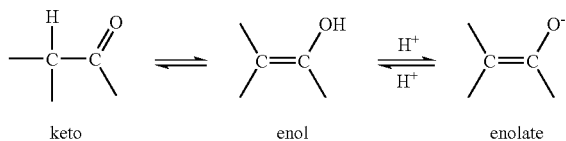

keto    enol    enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge, et al., J. Pharm. Sci., 66, 1-19 (1977).

For example, if the compound is anionic, or has a functional group which may be anionic (e.g. —COOH may be —COO⁻), then a salt may be formed with a suitable cation. Examples of suitable inorganic cations include, but are not limited to, alkali metal ions such as Na⁺ and K⁺, alkaline earth cations such as Ca²⁺ and Mg²⁺, and other cations such as Al⁺³. Examples of suitable organic cations include, but are not limited to, ammonium ion (i.e. $NH_4^+$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g. —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g. pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts; 3rd Edition; John Wiley and Sons, 1999).

A wide variety of such "protecting", "blocking", or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH₃, —OAc).

For example, an aldehyde or ketone group may be protected as an acetal (R—CH(OR)₂) or ketal (R₂C(OR)₂), respectively, in which the carbonyl group (>C=O) is converted to a diether (>C(OR)₂), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: an acetamide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O.).

For example, a carboxylic acid group may be protected as an ester for example, as: an C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

The term "treatment", as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "therapeutically-effective amount", as used herein, pertains to that amount of an active compound, or a material, composition or dosage form comprising an active compound, which is effective for producing some desired therapeutic effect, commensurate with a reasonable benefit/risk ratio, when administered in accordance with a desired treatment regimen. Suitable dose ranges will typically be in the range of from 0.01 to 20 mg/kg/day, preferably from 0.1 to 10 mg/kg/day.

Compositions and their Administration

Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. The active compound as defined above may be formulated as suppositories using, for example, polyalkylene glycols, acetylated triglycerides and the like, as the carrier. Liquid pharmaceutically administrable compositions can, for example, be prepared by dissolving, dispersing, etc, an active compound as defined above and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see Remington's Pharmaceutical Sciences, 20th edition, pub. Lippincott, Williams & Wilkins, 2000. The composition or formulation to be administered will, in any event, contain a quantity of the active compound(s) in an amount effective to alleviate the symptoms of the subject being treated.

Dosage forms or compositions containing active ingredient in the range of 0.25 to 95% with the balance made up from non-toxic carrier may be prepared.

For oral administration, a pharmaceutically acceptable non-toxic composition is formed by the incorporation of any of the normally employed excipients, such as, for example, pharmaceutical grades of mannitol, lactose, cellulose, cellulose derivatives, sodium crosscarmellose, starch, magnesium stearate, sodium saccharin, talcum, glucose, sucrose, magnesium carbonate, and the like. Such compositions take the form of solutions, suspensions, tablets, pills, capsules, powders, sustained release formulations and the like. Such compositions may contain 1%-95% active ingredient, more preferably 2-50%, most preferably 5-8%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, triethanolamine sodium acetate, etc.

The percentage of active compound contained in such parental compositions is highly dependent on the specific nature thereof, as well as the activity of the compound and the needs of the subject. However, percentages of active ingredient of 0.1% to 10% in solution are employable, and will be higher if the composition is a solid which will be subsequently diluted to the above percentages. Preferably, the composition will comprise 0.2-2% of the active agent in solution.

Acronyms

For convenience, many chemical moieties are represented using well known abbreviations, including but not limited to, methyl (Me), ethyl (Et), n-propyl (nPr), iso-propyl (iPr), n-butyl (nBu), sec-butyl (sBu), iso-butyl (iBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et$_2$O), acetic acid (AcOH), dichloromethane (methylene chloride, DCM), acetonitrile (ACN), trifluoroacetic acid (TFA), dimethylformamide (DMF), tetrahydrofuran (THF), and dimethylsulfoxide (DMSO).

General Synthesis Methods

Compounds of the invention wherein $R^3$ is of formula (II):

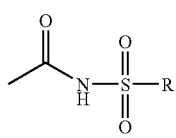
(II)

may be synthesised from the analogous compound of the invention wherein $R^3$ is carboxy, by reaction with a compound of formula 1:

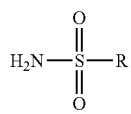
Formula 1 in basic conditions, preferably aided by a coupling agent, for example, 1-(3-dimethylaminopropyl)-3-ethylcarbodiimide hydrochloride.

Compounds of the invention wherein $R^3$ is of formula (III):

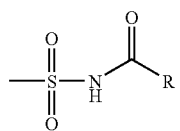
(III)

may be synthesized from a compound of formula 2:

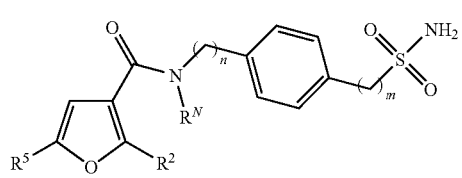
Formula 2 by reaction with a compound of formula 3:

Formula 3 wherein X is either OH or halo, where if X is OH, the use of basic conditions and a coupling agent is preferred.

Compounds where $R^3$ is tetrazol-5-yl may be synthesised from compounds of formula 4:

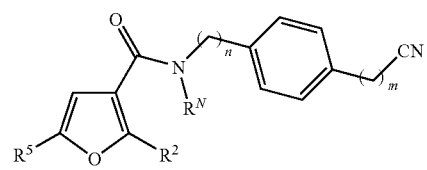
Formula 4 by treatment with sodium azide in the presence of a base. Compounds of formula 4 may be synthesised by coupling compounds of Formula 5 and Formula 6a.

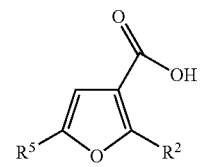
Formula 5

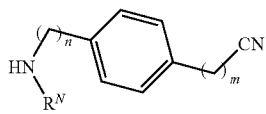
Formula 6a

Such a coupling step may be carried out using a coupling agent, for example, O-(7-azabenzotriazol-1-yl)-N,N,N',N'-tetramethyluronium hexafluorophosphate.

Compounds where $R^3$ is carboxy, may be synthesised from compounds of formula 7:

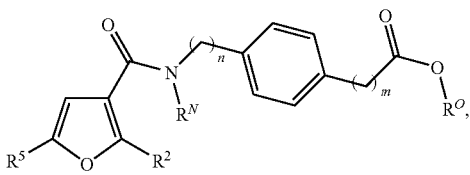
Formula 7 where $R^o$ is typically a $C_{1-4}$ alkyl group, by a hydrolysis reaction, for example, using sodium hydroxide.

Compounds of formula 7 can be synthesised by coupling compounds of formula 5 and 6b:

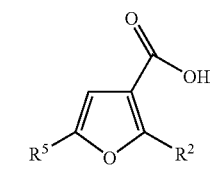
Formula 5

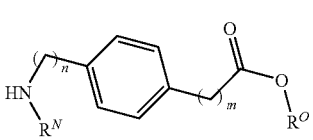
Formula 6b

Such a coupling step may be carried out as described above, by using a coupling agent, for example, O-(7-azabenzotriazol-1-yl)-N,N,N',N'-tetramethyluronium hexafluorophosphate.

In compounds of formula 5, if $R^5$ is an aryl group, then these may be synthesised from compounds of formula 8:

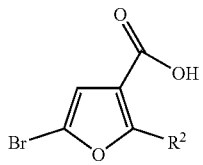

Formula 8 by a Suzuki coupling of a compound of formula 9a (or equivalent ester of formula 9b):

$R^5$—B(OH)$_2$       Formula 9a

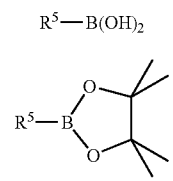

Formula 9b

The Suzuki coupling may be achieved using, for example, [1,1'-bis(diphenylphosphino)ferrocene]dichloropalladium (II) as the palladium catalyst.

Compounds of Formula 8 may be synthesised from compounds of formula 10:

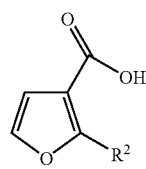

Formula 10 by treating the compound of formula 10 with a brominating agent, such as pyridinium tribromide.

Compounds where $R^2$ or $R^5$ is a phenyl group substituted by —O—CHF$_2$, can be synthesised from the corresponding compound where the phenyl group is substituted by —OH, by treating this compound with a base and chlorodifluoromethane.

Preferences

The following preferences may be combined with one another, and may be different for each aspect of the present invention.

$R^5$ is preferably the optionally substituted C5-7 aryl group and $R^2$ is preferably H or the optionally substituted $C_{1-4}$ alkyl group.

$R^2$ is preferably selected from H or an optionally substituted $C_{1-3}$ alkyl group, more preferably H, methyl, CF$_3$ or iso-propyl, and most preferably $R^2$ is a methyl group.

$R^5$ is preferably a $C_6$ aryl group, and is more preferably phenyl. $R^5$ may be substituted, and preferred substituents include $C_{1-7}$ alkoxy groups, more preferably $C_{1-4}$ alkoxy groups, e.g. —OMe, —OCF$_3$, —OEt, —OCHF$_2$, with —OCHF$_2$ being the most preferred.

$R^3$ is preferably either:
(i) a group of formula (II):

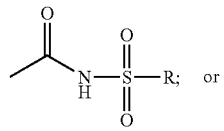

(ii) a group of formula (III):

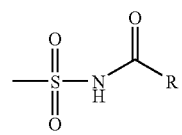

with a group of formula (II) being more preferred. In some embodiments, $R^3$ is preferably carboxy.

Where $R^3$ is of formula (II) or (III), R is preferably selected from an optionally substituted $C_{5-20}$ aryl group, and an optionally substituted $C_{5-20}$ aryl-$C_{1-7}$ alkyl group, wherein the $C_{1-7}$ alkyl group is more preferably methyl. In these groups the $C_{5-20}$ aryl group is preferably a $C_6$ aryl group. Such groups may preferably be substituted with $C_{1-4}$ alkyl groups, such as methyl and hydroxy or halo groups, for example, fluoro. Thus, preferred R groups include, but are not limited to: phenyl; benzyl; 2-fluoro-phenyl; 4-hydroxy-phenyl; 2-trifluoromethyl-phenyl; 5-methyl-pyrid-2-yl.

If R in formula (II) or (III) is a $C_{1-7}$ alkyl group, it is more preferably a $C_{1-4}$ alkyl group, for example methyl or propyl.

Preferably n+m=1, and more preferably n is 0 and m is 1.

$R^N$ is preferably H or methyl, and is more preferably H.

Particularly preferred compounds of the present invention include:
- (4-{[5-(4-Methoxy-phenyl)-2-trifluoromethyl-furan-3-carbonyl]-amino}-phenyl)-acetic acid (4);
- (4-{[5-(4-Methoxy-phenyl)-2-methyl-furan-3-carbonyl]-amino}-phenyl)-acetic acid (6);
- {4-[(5-Phenyl-furan-3-carbonyl)-amino]-phenyl}-acetic acid (10);
- (4-{[5-(4-Difluoromethoxy-phenyl)-furan-3-carbonyl]-amino}-phenyl)-acetic acid (13);
- (4-{[5-(4-Difluoromethoxy-phenyl)-2-methyl-furan-3-carbonyl]-amino}-phenyl)-acetic acid (18);
- 4-{[(5-Methyl-2-phenyl-furan-3-carbonyl)-amino]-methyl}-benzoic acid (20);
- 2-Methyl-5-phenyl-furan-3-carboxylic acid [4-(2-benzenesulfonylamino-2-oxo-ethyl)-phenyl]-amide (21);
- 5-(4-Methoxy-phenyl)-2-trifluoromethyl-furan-3-carboxylic acid [4-(2-benzenesulfonylamino-2-oxo-ethyl)-phenyl]-amide (22);
- 5-(4-Methoxy-phenyl)-2-methyl-furan-3-carboxylic acid [4-(2-benzenesulfonylamino-2-oxo-ethyl)-phenyl]-amide (23);
- 5-Phenyl-furan-3-carboxylic acid {4-[2-oxo-2-(toluene-2-sulfonylamino)-ethyl]-phenyl}-amide (24);
- 5-(4-Difluoromethoxy-phenyl)-2-methyl-furan-3-carboxylic acid [4-(2-benzenesulfonylamino-2-oxo-ethyl)-phenyl]-amide (25);
- 5-(4-Difluoromethoxy-phenyl)-2-methyl-furan-3-carboxylic acid {4-[2-oxo-2-(toluene-2-sulfonylamino)-ethyl)-phenyl}-amide (26);

5-(4-Difluoromethoxy-phenyl)-2-methyl-furan-3-carboxylic acid {4-[2-oxo-2-(propane-1-sulfonylamino)-ethyl]-phenyl}-amide (27);

5-(4-Difluoromethoxy-phenyl)-2-methyl-furan-3-carboxylic acid {4-[2-(3,5-dimethyl-isoxazole-4-sulfonylamino)-2-oxo-ethyl]-phenyl}-amide (28);

5-(4-Difluoromethoxy-phenyl)-2-methyl-furan-3-carboxylic acid {4-[2-oxo-2-(thiophene-2-sulfonylamino)-ethyl]-phenyl}-amide (29);

5-(4-Difluoromethoxy-phenyl)-2-methyl-furan-3-carboxylic acid {4-[2-(5-methyl-pyridine-2-sulfonylamino)-2-oxo-ethyl]-phenyl}-amide (30);

5-(4-Difluoromethoxy-phenyl)-2-methyl-furan-3-carboxylic acid [4-(2-oxo-2-phenylmethanesulfonylamino-ethyl)-phenyl]-amide (31);

5-(4-Difluoromethoxy-phenyl)-2-methyl-furan-3-carboxylic acid {4-[2-oxo-2-(2-trifluoromethyl-benzenesulfonylamino)-ethyl]-phenyl}-amide (32);

5-(4-Difluoromethoxy-phenyl)-2-methyl-furan-3-carboxylic acid {4-[2-(4-hydroxy-benzenesulfonylamino)-2-oxo-ethyl]-phenyl}-amide (35); and 5-(4-Difluoromethoxy-phenyl)-2-methyl-furan-3-carboxylic acid {4-[2-(2-fluoro-benzenesulfonylamino)-2-oxo-ethyl]-phenyl}-amide (36).

The selectivity of the compound for antagonising $EP_4$ receptors over the other EP receptors (i.e. $EP_1$, $EP_2$, $EP_3$) can be quantified by dividing the Ki for $EP_4$ (see below) by the Ki for the other EP receptors (see below). The resulting ratio is preferably 10 or more, more preferably 100 or more.

SYNTHESIS EXAMPLES

General Experimental Details

All reactions were carried out under an inert atmosphere of nitrogen.

Where products were purified by flash chromatography the stationary phase used was silica gel for chromatography, 0.035 to 0.070 mm (220 to 440 mesh) (e.g. Fluka silica gel 60). An applied pressure of nitrogen of ~10 psi was used to accelerate column elution. Thin layer chromatography (TLC) was carried out on aluminium foil plates coated with silica gel containing a fluorescent indicator (254 nm) (e.g. Fluka 60778).

Petroleum ether refers to that fraction with a boiling point of 40-60° C.

Organic solutions were dried over magnesium sulphate unless otherwise specified.

PS-TsCl refers to Polystyrene scavenger resin (loading 1.97 mmol/g)—Argonaut Technologies (P/N 800277)

Preparative HPLC System

Preparative HPLC was carried out on a C18-reverse-phase column (10×2.1 cm i.d Genesis column with 7 μm particle size), eluting with a gradient of acetonitrile (containing 0.1% trifluoroacetic acid) in water (containing 0.1% trifluoroacetic acid) at a flow rate of 5 ml/min. The gradient was started at 50% acetonitrile, and was increased at a rate of 1% per minute up to 90% acetonitrile/water unless otherwise stated. UV detection at 230 nm was used unless otherwise stated.

LC/MS Systems

The Liquid Chromatography Mass Spectroscopy (LC/MS) systems used are as follows.

LC/MS System A:

Mass Spectrometer—Platform LC with electrospray source operating in positive and negative ion mode. HP1100 system running at 2.0 mL/min, 200 μL/min split to the ESI source with inline HP1100 DAD detection and SEDEX ELS detection.

Mobile Phase
A) Water 0.1% Formic Acid
B) acetonitrile 0.1% Formic Acid

| | Gradient | | |
|---|---|---|---|
| Time (min) | Flow (mL/min) | % A | % B |
| 0.00 | 2.0 | 95 | 5 |
| 0.50 | 2.0 | 95 | 5 |
| 4.50 | 2.0 | 5 | 95 |
| 5.00 | 2.0 | 5 | 95 |
| 5.50 | 2.0 | 95 | 5 |

Column—Luna 3 u C18(2) 30×4.6 mm

LC/MS System B:

Mass Spectrometer—Platform II with electrospray source operating in negative ion mode. HP1100 system running at 2.0 mL/min, 200 μL/min split to the ESI source with inline HP1100 DAD detection and SEDEX ELS detection.

Mobile Phase
A) Water 0.1% Diethylamine
B) acetonitrile

| | Gradient | | |
|---|---|---|---|
| Time (min) | Flow (mL/min) | % A | % B |
| 0.00 | 2.0 | 95 | 5 |
| 0.50 | 2.0 | 95 | 5 |
| 4.00 | 2.0 | 5 | 95 |
| 4.50 | 2.0 | 5 | 95 |
| 5.00 | 2.0 | 95 | 5 |
| 20.00 | 2.0 | 95 | 5 |

Column—XTerra MS C18 3.5 μm 4.6×30 mm

LCMS System C:

Mass Spectrometer—Finnigan TSQ700 with electrospray source operating in negative ion mode. HP1050 system running at 2.0 mL/min, 200 μL/min split to the ESI source with inline HP1050 Single wavelength UV detector at 254 nm.

Mobile Phase
A) Water 0.1% Diethylamine
B) acetonitrile

| | Gradient | | |
|---|---|---|---|
| Time (min) | Flow (mL/min) | % A | % B |
| 0.00 | 2.0 | 95 | 5 |
| 1.00 | 2.0 | 95 | 5 |
| 15.00 | 2.0 | 5 | 95 |
| 17.00 | 2.0 | 5 | 95 |
| 18.00 | 2.0 | 95 | 5 |
| 20.00 | 2.0 | 95 | 5 |

Column—XTerra MS C18 3.5 μm 4.6×30 mm

LC/MS System D:

Mass Spectrometer—Finnigan TSQ700 with electrospray source operating in positive or negative ion mode. HP1050 system running at 2.0 mL/min, 200 μL/min split to the ESI source with inline HP1050 Single Wavelength UV detector at 254 nm.

Mobile Phase

A) Water 0.1% formic Acid

B) acetonitrile 0.1% formic Acid

| Gradient | | | |
|---|---|---|---|
| Time (min) | Flow (mL/min) | % A | % B |
| 0.00 | 2.0 | 95 | 5 |
| 1.00 | 2.0 | 95 | 5 |
| 15.00 | 2.0 | 5 | 95 |
| 17.00 | 2.0 | 5 | 95 |
| 18.00 | 2.0 | 95 | 5 |
| 20.00 | 2.0 | 95 | 5 |

Column—Higgins Clipius C18 5 μm 100×3.0 mm

Example 1

Synthesis of [(alkyl-phenyl-furan-3-carbonyl)-amino]-phenyl-acetic acids (a) {4-[(2-Methyl-5-phenyl-furan-3-carbonyl)-amino]-phenyl}-acetic acid (2)

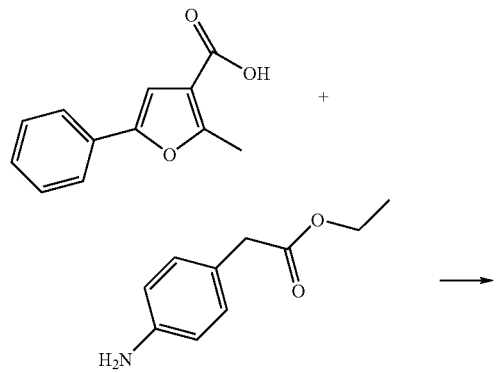

1

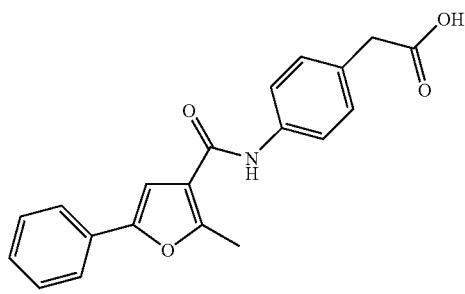

2

(i) Diisopropylethylamine (427 mg) was added to a stirred solution of 2-methyl-5-phenyl-furan-3-carboxylic acid (334 mg, 1.6 mmol) and ethyl-4-aminophenyl acetate (296 mg, 1.65 mmoles) in N,N-dimethylformamide (30 ml). 0-(7-Azabenzotriazol-1-yl)-N,N,N',N'-tetramethyluronium hexafluorophosphate (628 mg, 1.65 mmoles) was added and the solution was stirred at room temperature for 18 hours. The solvent was evaporated, the residue was dissolved in dichloromethane and washed with water, 10% aqueous sodium carbonate, 1M aqueous hydrochloric acid and finally dried ($MgSO_4$). After evaporation of the solvent, the residue was triturated with cyclohexane and dried to afford (4-[(2-Methyl-5-phenyl-furan-3-carbonyl)-amino]-phenyl}-acetic acid ethyl ester (1)(466 mg) as a gum. LC/MS System D; $R_t$=10.64 mins, m/z ($ES^+$)=364 (M+H for $C_{22}H_{21}NO_4$).

(ii) A solution of sodium hydroxide (150 mg) in water (5 ml) was added to a stirred solution of {4-[(2-methyl-5-phenyl-furan-3-carbonyl)-amino]-phenyl}-acetic acid ethyl ester (1) (150 mg, 0.41 mmoles) in ethanol (20 ml) and the mixture was stirred at room temperature for 1 hour. The solvent was evaporated and the residue was diluted with water (10 ml) and acidified to pH2 with 1M aqueous hydrochloric acid. The precipitate was collected, washed with water and the residue was triturated with cyclohexane. Recrystallisation from isopropanol afforded compound (2)(135 mg) as a white solid. LC/MS System C; $R_t$=4.06 mins, m/z ($ES^-$)=334 (M–H for $C_{20}H_{17}NO_4$).

(b) (4-([5-(4-Methoxy-phenyl)-2-trifluoromethyl-furan-3-carbonyl]-amino}-phenyl)-acetic acid (4)

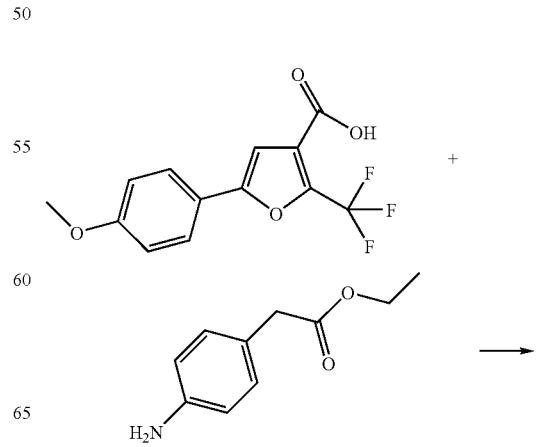

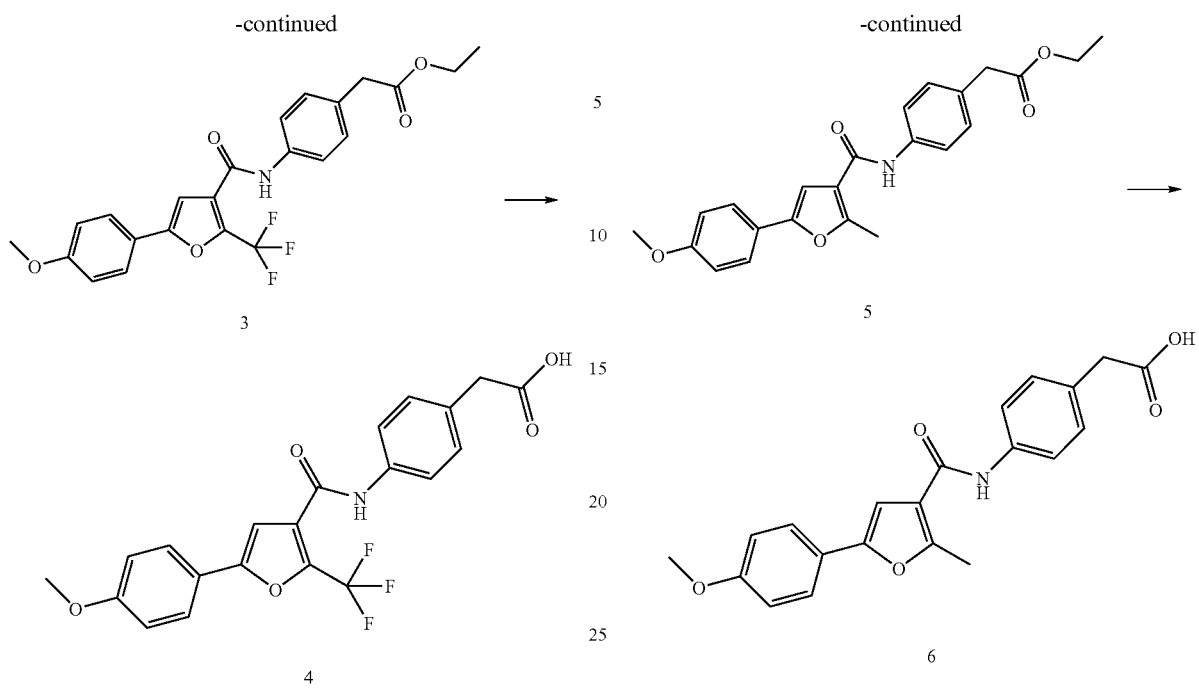

(i) In an analogous manner to example 1(a)(i), (4-{[5-(4-Methoxy-phenyl)-2-trifluoromethyl-furan-3-carbonyl]-amino}-(phenyl)-acetic acid ethyl ester (3) was synthesised from 5-(4-methoxy-phenyl)-2-trifluoromethyl-furan-3-carboxylic acid (160 mg, 0.56 mmol) and ethyl-4-aminophenyl acetate (100 mg, 0.56 mmoles). 190 mg of the product was obtained as a gum. LC/MS System A; $R_t$=4.15 mins, m/z (ES$^+$)=448 (M+H for $C_{23}H_{20}F_3NO_5$).

(ii) In an analogous manner to example 1(a)(ii), compound (4), was synthesised from (4-{[5-(4-methoxy-phenyl)-2-trifluoromethyl-furan-3-carbonyl]-amino}-phenyl)-acetic acid ethyl ester (3) (180 mg, 0.403 mmoles). The resulting precipitate was collected, washed with water and the residue was triturated with cyclohexane to afford compound (4) (140 mg) as a white solid. LC/MS System D; $R_t$=8.07 mins, m/z (ES$^+$)=420 (M+H for $C_{21}H_{16}F_3NO_5$).

(c) (4-([5-(4-Methoxy-phenyl)-2-methyl-furan-3-carbonyl]-amino]-phenyl)-acetic acid (6)

(i) In an analogous manner to example 1(a)(i), (4-([5-(4-Methoxy-phenyl)-2-methyl-furan-3-carbonyl]-amino)-phenyl)-acetic acid ethyl ester (5) was synthesised from 5-(4-methoxy-phenyl)-2-methyl-furan-2-carboxylic acid (250 mg, 1.077 mmol) and ethyl-4-aminophenyl acetate (193 mg, 1.077 mmoles). 80 mg of the compound was obtained as a gum. LC/MS System A; $R_t$=4.03 mins, m/z (ES$^+$)=394 (M+H for $C_{23}H_{23}NO_5$).

(ii) In an analogous manner to example 1(a)(ii), compound (6), was synthesised from {4-[(5-phenyl-furan-3-carbonyl)-amino]-phenyl}-acetic acid ethyl ester (5) (50 mg, 0.143 mmoles). The resulting precipitate was collected, washed with water and the residue was triturated with cyclohexane to afford compound (6)(14 mg) as a white solid. LC/MS System D; $R_t$=7.25 mins, m/z (ES$^+$)=322 (M+H for $C_{19}H_{15}NO_4$).

(d) (4-[(5-Phenyl-furan-3-carbonyl)-amino]-phenyl}-acetic acid (10)

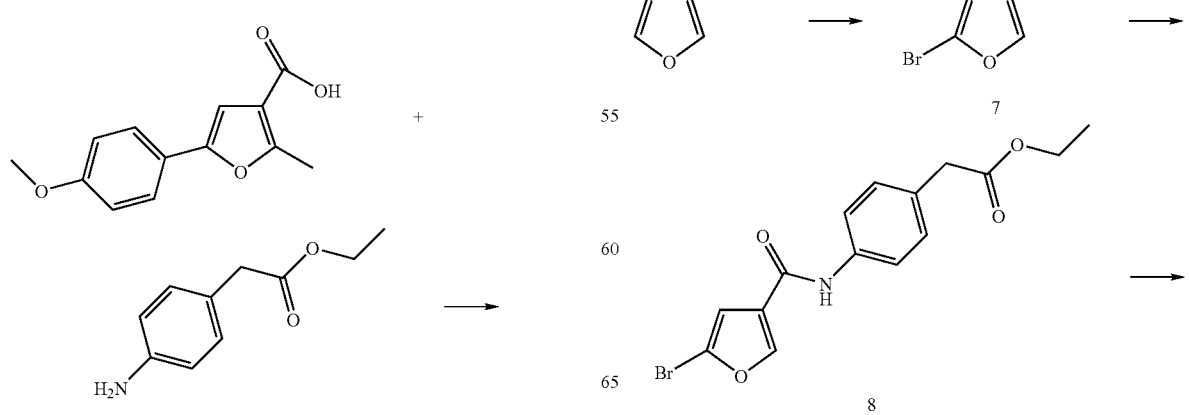

-continued

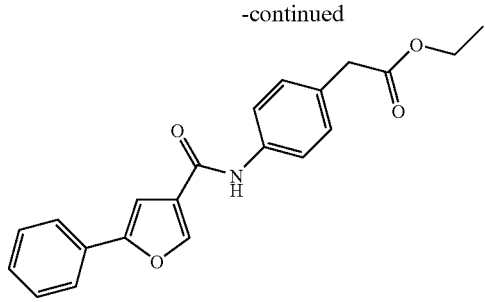

9

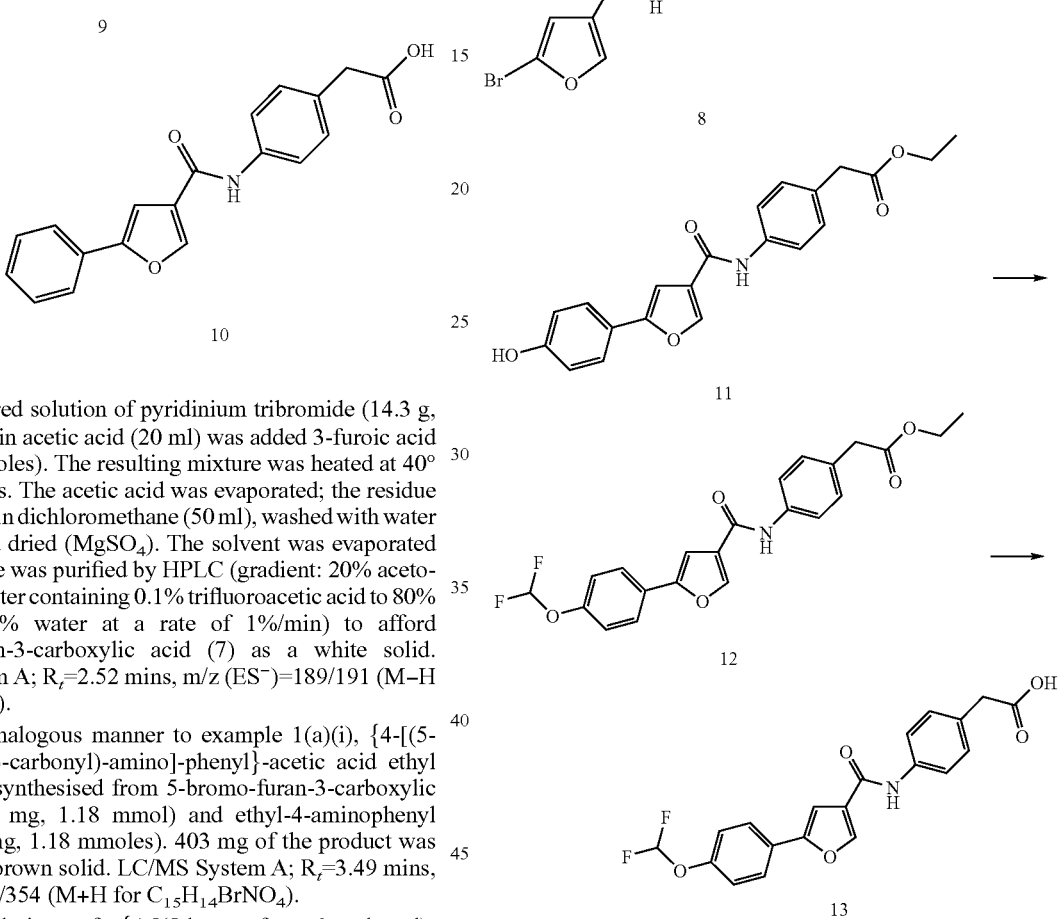

(i) To a stirred solution of pyridinium tribromide (14.3 g, 44.6 mmoles) in acetic acid (20 ml) was added 3-furoic acid (5 g, 44.6 mmoles). The resulting mixture was heated at 40° C. for 16 hours. The acetic acid was evaporated; the residue was dissolved in dichloromethane (50 ml), washed with water (3×50 ml) and dried (MgSO$_4$). The solvent was evaporated and the residue was purified by HPLC (gradient: 20% acetonitrile/80% water containing 0.1% trifluoroacetic acid to 80% acetonitrile/20% water at a rate of 1%/min) to afford 5-Bromo-furan-3-carboxylic acid (7) as a white solid. LC/MS System A; R$_t$=2.52 mins, m/z (ES$^-$)=189/191 (M−H for C$_5$H$_3$BrO$_3$).

(ii) In an analogous manner to example 1(a)(i), {4-[(5-bromo-furan-3-carbonyl)-amino]-phenyl}-acetic acid ethyl ester (8) was synthesised from 5-bromo-furan-3-carboxylic acid (7) (225 mg, 1.18 mmol) and ethyl-4-aminophenyl acetate (213 mg, 1.18 mmoles). 403 mg of the product was obtained as a brown solid. LC/MS System A; R$_t$=3.49 mins, m/z (ES$^+$) 352/354 (M+H for C$_{15}$H$_{14}$BrNO$_4$).

(iii) A solution of {4-[(5-bromo-furan-3-carbonyl)-amino]-phenyl}-acetic acid ethyl ester (8) (200 mg, 0.57 mmoles), phenyl boronic acid (69.2 mg, 0.57 mmoles), [1,1'-bis(diphenylphosphino)ferrocene]dichloropalladium(II) (50 mg, 0.06 mmoles) and 2M aqueous cesium carbonate (1.2 ml, 2.4 mmoles) in toluene (20 ml) was refluxed for 16 hours. The solvent was evaporated, the residue diluted with water (20 ml) and then extracted with ethyl acetate (3×20 ml). The combined organic layers were concentrated in vacuo. The residue was was purified by flash chromatography (gradient elution with 90% cyclohexane/10% ethyl acetate to 50% cyclohexane/50% ethyl acetate) to afford {4-[(5-phenyl-furan-3-carbonyl)-amino]-phenyl}-acetic acid ethyl ester (9) (53 mg). LC/MS System A; R$_t$=3.84 mins, m/z (ES$^+$)=(M+H for C$_{21}$H$_{19}$NO$_4$).

(iv) In an analogous manner to example 1(a)(ii), compound (10), was synthesised from {4-[(5-phenyl-furan-3-carbonyl)-amino]-phenyl}-acetic acid ethyl ester (9) (50 mg, 0.143 mmoles). The resulting precipitate was collected, washed with water and the residue was triturated with cyclohexane to afford compound (10) (14 mg) as a white solid. LC/MS System D; R$_t$=7.25 mins, m/z (ES$^+$)=322 (M+H for C$_{19}$H$_{15}$NO$_4$).

(e) (4-{[5-(4-Difluoromethoxy-phenyl)-furan-3-carbonyl]-amino}-phenyl)-acetic acid (13)

(i) A solution of {4-[(5-Bromo-furan-3-carbonyl)-amino]-phenyl}-acetic acid ethyl ester (828 mg, 2.35 mmoles) (8), 4-(4,4,5,5-tetramethyl-[1,3,2]dioxaborolan-2-yl)-phenol (518 mg, 2.35 mmoles), [1,1'-bis(diphenylphosphino)ferrocene]dichloropalladium(II) (50 mg) and 2M aqueous cesium carbonate (3.5 ml, 3.5 mmoles) in N,N-dimethylformamide (20 ml) was heated in a microwave reactor at 100° C. for 15 minutes. The solvent was evaporated, and the residue was purified by flash chromatography (gradient elution with 100% cyclohexane to 50% cyclohexane/50% ethyl acetate) to afford (4-{[5-(4-hydroxy-phenyl)-furan-3-carbonyl]-amino}-phenyl)-acetic acid ethyl ester (11) (328 mg). LC/MS System A; R$_t$=3.35 mins, m/z (ES$^+$)=366 (M+H for C$_{21}$H$_{19}$NO$_5$).

(ii) To a stirred solution of (4-{[5-(4-hydroxy-phenyl)-furan-3-carbonyl]-amino}-phenyl)-acetic acid ethyl ester (328 mg, 0.898 mmoles) (11) in N,N-dimethylformamide (15 ml) was added potassium carbonate (190 mg, 1.35 mmoles) and potassium iodide (75 mg, 0.449 mmoles). Chlorodifluoromethane was bubbled through the solution at 80° C. for 5 hours, and then discontinued. The reaction mixture was stirred at 80° C. for 16 hours. The reaction was cooled to room temperature and quenched by the addition of water until no effervescence was observed. The resulting solution was extracted with ethyl acetate and the combined organic layers washed with brine, dried over MgSO$_4$ and concentrated in vacuo. The residue was purified by flash chromatography (gradient: 100% cyclohexane to 50% cyclohexane/50% ethyl acetate) to afford (4-{[5-(4-Difluoromethoxy-phenyl)-furan-3-carbonyl]-amino}-phenyl)-acetic acid ethyl ester (12)(60 mg) as a yellow solid. LC/MS System A; R$_t$=3.91 mins, m/z (ES$^+$)=416 (M+H for C$_{22}$H$_{19}$F$_2$NO$_5$).

(iii) In an analogous manner to example 1(a)(ii), compound (13), was synthesised from (4-{[5-(4-difluoromethoxy-phenyl)-furan-3-carbonyl]-amino}-phenyl)-acetic acid ethyl ester (12) (55 mg, 0.132 mmoles). The resulting precipitate was collected, washed with water and the residue was triturated with cyclohexane to afford the compound (13)(41.8 mg) as a white solid. LC/MS System D; R$_t$=8.86 mins, m/z (ES$^+$)=388 (M+H for C$_2$H$_{15}$ F$_2$NO$_5$).

(f) (4-{[5-(4-Difluoromethoxy-phenyl)-furan-3-carbonyl]-amino}-phenyl)-acetic acid (18)

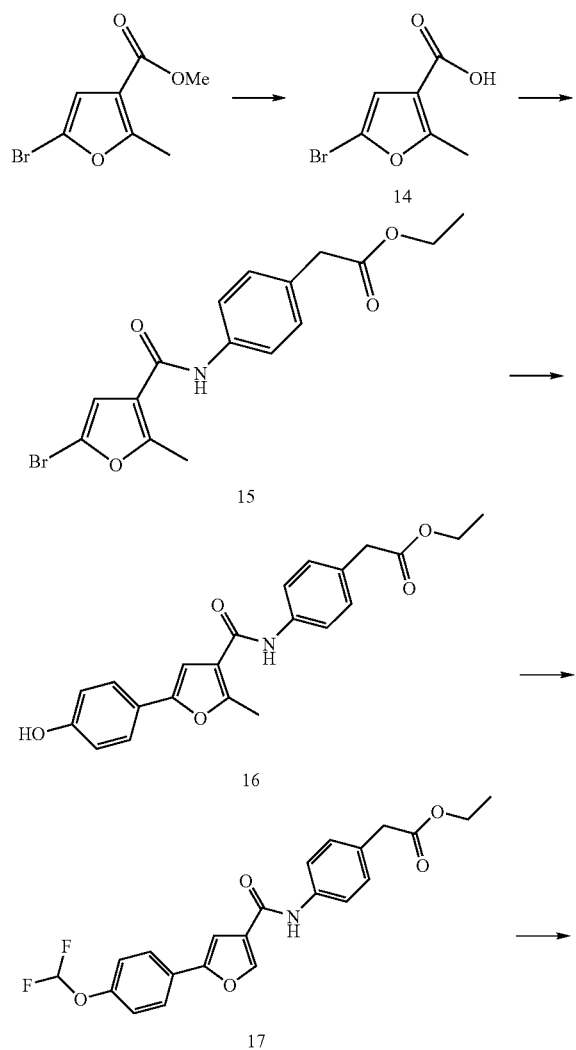

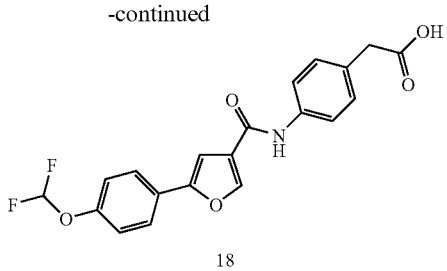

(i) A solution of sodium hydroxide (4.5 g) in water (10 ml) was added to a stirred solution of 5-bromo-2-methyl-furan-3-carboxylic acid methyl ester (5 g, 233 mmoles) in methanol (70 ml) and the mixture was stirred at room temperature for 16 hours. The solvent was evaporated and the residue was diluted with water (10 ml) and acidified to pH2 with 1M aqueous hydrochloric acid. The precipitate was collected, washed with water, dried at 40° C. to afford 5-Bromo-2-methyl-furan-3-carboxylic acid (14)(4 g). LC/MS System A; R$_t$=2.86 min.

(ii) In an analogous manner to example 1(a)(i), {4-[(5-bromo-2-methyl-furan-3-carbonyl)-amino)-phenyl}-acetic acid ethyl ester (15) was synthesised from 5-bromo-2-methyl-furan-3-carboxylic acid (14) (1.8 g, 8.78 mmoles) and (4-amino-phenyl)-acetic acid ethyl ester(1.6 g, 8.9 mmoles). 3.08 g of the product was obtained as a gum. LC/MS System A; R$_t$=3.73 mins, m/z (ES$^+$)=367 (M+H for C$_{16}$H$_{16}$BrNO$_4$).

(iii) A solution of {4-((5-bromo-2-methyl-furan-3-carbonyl)-amino]-phenyl}-acetic acid ethyl ester (3 g, 8.19 mmoles) (15), 4-(4,4,5,5-Tetramethyl-[1,3,2]dioxaborolan-2-yl)-phenol (1.8 g, 8.19 mmoles), [1,1'-bis(diphenylphosphino)ferrocene]dichloropalladium(II) (300 mg, 10%) and 2M aqueous cesium carbonate (15 ml, 15 mmoles) in N,N-dimethylformamide (35 ml) was heated in a microwave reactor at 100° C. for 15 minutes. The solvent was evaporated, and the residue was purified by flash chromatography (gradient elution with 100% cyclohexane to 100% ethyl acetate) to afford (4-{[5-(4-hydroxy-phenyl)-2-methyl-furan-3-carbonyl]-amino}-phenyl)-acetic acid ethyl ester (16) (1.9 g). LC/MS System A; R$_t$=3.54 mins, m/z (ES$^+$)=380 (M+H for C$_{22}$H$_{21}$NO$_5$).

(iv) To a stirred solution of (4-{[5-(4-hydroxy-phenyl)-2-methyl-furan-3-carbonyl]-amino}-phenyl)-acetic acid ethyl ester (1.9 g, 5 mmoles) (16) in N,N-dimethylformamide (70 ml) was added potassium carbonate (1.04 g, 7.5 mmoles) and potassium iodide (416 mg, 2.5 mmoles). Chlorodifluoromethane was bubbled through the solution at 80° C. for 5 hours, and then discontinued. The reaction mixture was stirred at 80° C. for 16 hours. The reaction was cooled to room temperature and quenched by the addition of water until no effervescence was observed. The resulting solution was extracted with ethyl acetate (3×150 ml) and the combined organic layers washed with brine (200 ml), dried over MgSO$_4$ and concentrated in vacuo. The residue was purified by flash chromatography (gradient: 100% cyclohexane to 50% cyclohexane/50% ethyl acetate) to afford (4-{[5-(4-difluoromethoxy-phenyl)-2-methyl-furan-3-carbonyl]-amino}-phenyl)-acetic acid ethyl ester (17)(694 mg) as a white solid. LC/MS System A; R$_t$4.13 mins, m/z (ES$^+$)=430 (M+H for C$_{23}$H$_{21}$F$_2$NO$_5$).

(v) In an analogous manner to example 1(a)(ii), compound (18), was synthesised from (4-{[5-(4-difluoromethoxy-phenyl)-2-methyl-furan-3-carbonyl]-amino}-phenyl)-acetic acid ethyl ester (17) (694 mg, 1.62 mmoles). The resulting precipitate was collected, washed with water and the residue was triturated with cyclohexane to afford compound (18) (643 mg) as a white solid. LC/MS System D; $R_t$=9.46 mins, m/z (ES$^+$)=402 (M+H for $C_{21}H_{17}F_2NO_5$).

Example 2

Synthesis of 4-{[(5-Methyl-2-phenyl-furan-3-carbonyl)-amino]-methyl}-benzoic acid (20)

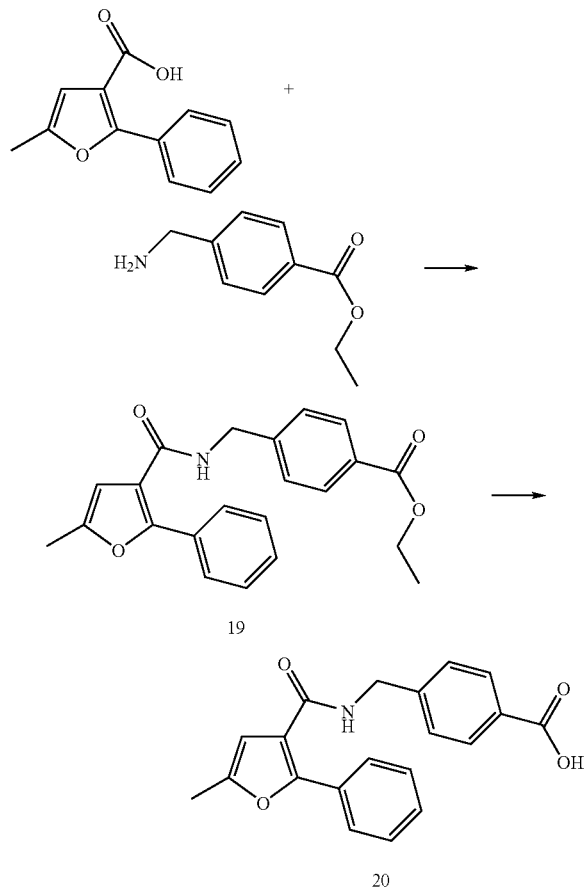

(i) In an analogous manner to example 1(a)(i), 4-{[(5-methyl-2-phenyl-furan-3-carbonyl)-amino]-methyl}-benzoic acid ethyl ester (19) was synthesised from 5-methyl-2-phenyl-furan-3-carboxylic acid (79 mg, 0.39 mmol) and 4-aminomethyl benzoic acid ethyl ester (70 mg, 0.39 mmoles). 99 mg of the product was obtained as a gum. LC/MS System A; $R_t$=3.88 mins, m/z (ES$^+$)=364 (M+H for $C_{22}H_{21}NO_4$).

(ii) In an analogous manner to example 1(a)(ii), compound (20), was synthesised from 4-{[(5-methyl-2-phenyl-furan-3-carbonyl)-amino]-methyl}-benzoic acid ethyl ester (19) (90 mg, 0.247 mmoles). The resulting precipitate was collected, washed with water and the residue was triturated with cyclohexane to afford compound (20)(51 mg) as a white solid. LC/MS System D; $R_t$=6.82 mins, m/z (ES$^+$)=336 (M+H for $C_{20}H_{17}NO_4$).

Example 3

Synthesis of alkyl-phenyl-furan-3-carboxylic acid [4-(2-sulphonylamino-2-oxo-ethyl)-phenyl] amides (a) 2-Methyl-5-phenyl-furan-3-carboxylic acid [4-(2-benzenesulfonylamino-2-oxo-ethyl)-phenyl]-amide (21)

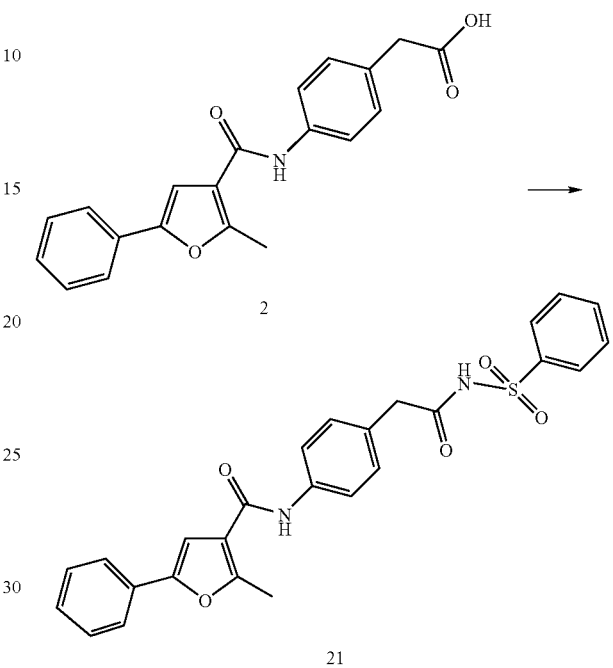

A stirred solution of {4-[(2-methyl-5-phenyl-furan-3-carbonyl)-amino]-phenyl}-acetic acid (2) (10 mg, 0.030 mmoles), 1-(3-dimethylaminopropyl)-3-ethylcarbodiimide hydrochloride (5.7 mg, 0.030 mmoles), and 4-(N,N-dimethylamino)-pyridine (3.5 mg) in dichloromethane (10 ml), was treated with benzenesulphonamide (9 mg, 0.060 mmoles). The mixture was stirred at room temperature for 18 hours. The reaction mixture was concentrated in vacuo and the residue was dissolved in ethyl acetate, washed with 0.1M aqueous hydrochloric acid, and brine and finally dried (MgSO$_4$). After evaporation of the solvent, the residue was purified by HPLC (gradient: 20% acetonitrile/80% water containing 0.1% trifluoroacetic acid to 80% acetonitrile/20% water at a rate of 1%/min) to afford compound (21)(10 mg) as a white solid. LC/MS System D; $R_t$=9.98 mins, m/z (ES$^+$)=475 (M+H for $C_{26}H_{22}N_2O_5S$).

(b) 5-(4-Methoxy-phenyl)-2-trifluoromethyl-furan-3-carboxylic acid [4-(2-benzenesulfonylamino-2-oxo-ethyl)-phenyl]-amide (22)

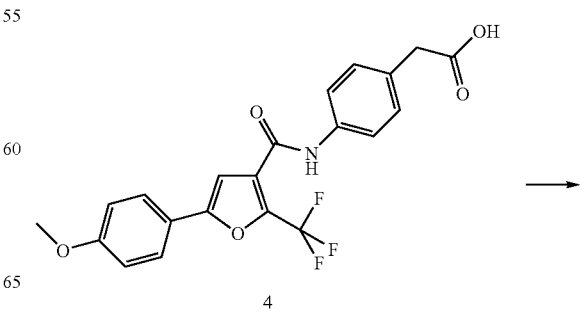

-continued

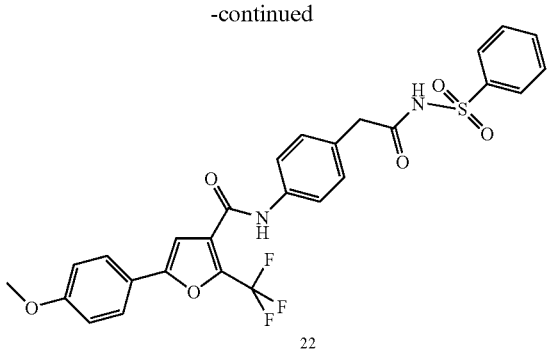

22

In an analogous way to example 3(a), compound (22) was synthesised from (4-{[5-(4-methoxy-phenyl)-2-trifluoromethyl-furan-3-carbonyl]-amino}-phenyl)-acetic acid (4) (40 mg, 0.095 mmoles). The reaction mixture was concentrated in vacuo and the residue was dissolved in dichloromethane, washed with 0.1M aqueous hydrochloric acid, and brine and finally dried (MgSO$_4$). After evaporation of the solvent, the residue was triturated with cyclohexane and a white solid filtered off, which was purified by HPLC (gradient: 20% acetonitrile/80% water containing 0.1% trifluoroacetic acid to 80% acetonitrile/20% water at a rate of 1%/min) to afford compound (22) (12 mg) as a white solid. LC/MS System D; R$_t$=9.08 mins, m/z (ES$^+$)=559 (M+H for C$_{27}$H$_{21}$F$_3$N$_2$O$_6$S).

(c) 5-(4-Methoxy-phenyl)-2-methyl-furan-3-carboxylic acid [4-(2-benzenesulfonylamino-2-oxo-ethyl)-phenyl]-amide (23)

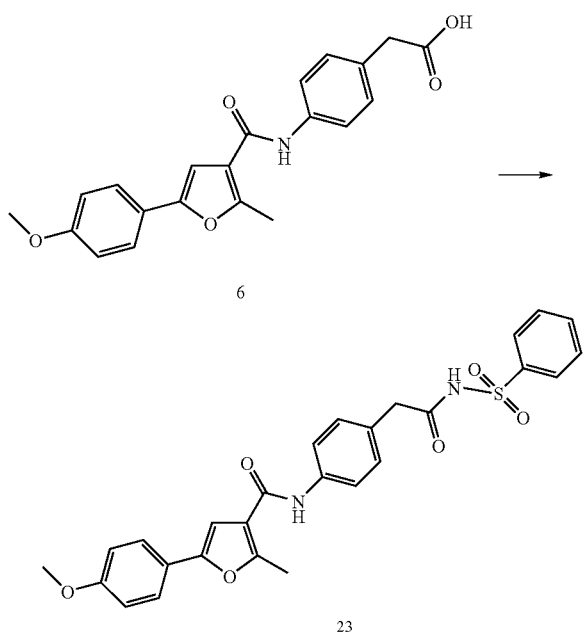

In an analogous way to example 3(a), compound (23) was synthesised from (4-{[5-(4-methoxy-phenyl)-2-methyl-furan-3-carbonyl]-amino}-phenyl)-acetic acid (6) (100 mg, 0.273 mmoles). The reaction mixture was concentrated in vacuo and the residue was dissolved in dichloromethane, washed with 0.1M aqueous hydrochloric acid, and brine and finally dried (MgSO$_4$). After evaporation of the solvent, the residue was triturated with cyclohexane and a white solid filtered off, which was then purified by HPLC (gradient: 20% acetonitrile/80% water containing 0.1% trifluoroacetic acid to 80% acetonitrile/20% water at a rate of 1%/min) to afford compound (23)(50 mg) as a white solid. LC/MS System D; R$_t$=8.58 mins, m/z (ES$^+$)=405 (M+H for C$_{27}$H$_{24}$N$_2$O$_6$S).

(d) 5-Phenyl-furan-3-carboxylic acid {4-[2-oxo-2-(toluene-2-sulfonylamino)-ethyl]-phenyl}-amide (24)

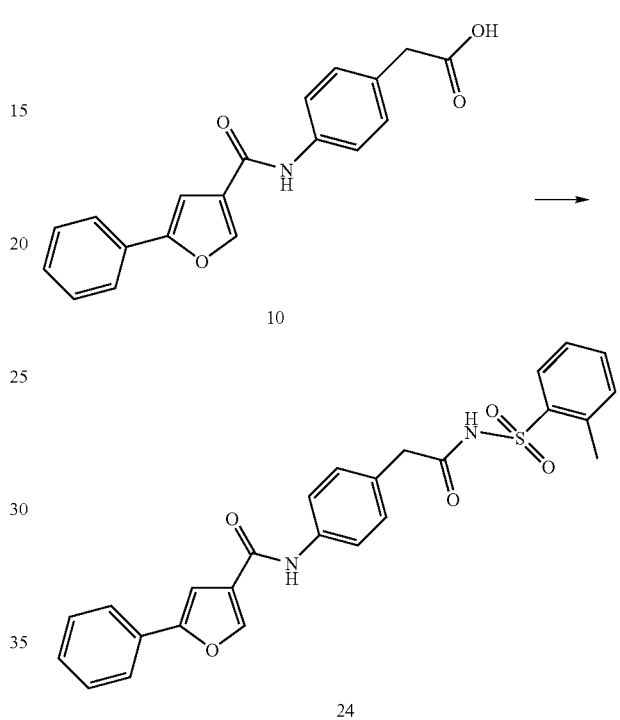

In an analogous way to example 3(a), compound (24) was synthesised from {4-[(5-phenyl-furan-3-carbonyl)-amino]-phenyl}-acetic acid (10) (40 mg, 0.125 mmoles) and replacing benzene-sulfonamide with toluene-2-sulfonamide. The reaction mixture was concentrated in vacuo and the residue purified by HPLC (gradient: 20% acetonitrile/80% water containing 0.1% trifluoroacetic acid to 80% acetonitrile/20% water at a rate of 1%/min) to afford compound (24)(4 mg) as an off-white solid. LC/MS System D; R$_t$=9.85 mins, m/z (ES$^+$)=475 (M+H for C$_{26}$H$_{22}$N$_2$O$_5$S).

(e) Compounds derived from (4-{[5-(4-Difluoromethoxy-phenyl)-2-methyl-furan-3-carbonyl]-amino}-phenyl)-acetic acid (18)

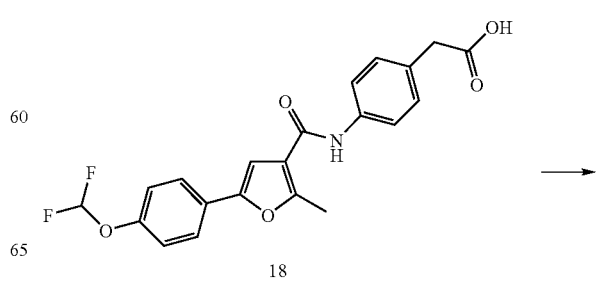

18

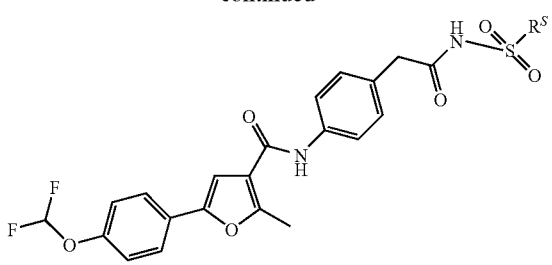

A stirred solution of (4-{[5-(4-difluoromethoxy-phenyl)-2-methyl-furan-3-carbonyl]-amino}-phenyl)-acetic acid (18) (20 mg, 0.050 mmoles), 1-(3-dimethylaminopropyl)-3-ethylcarbodiimide hydrochloride (19.1 mg, 0.010 mmoles), and 4-(N,N-dimethylamino)-pyridine (6 mg, 0.050 mmoles) in dichloromethane (10 ml), was treated with a sulphonamide ($R^S S(=O)_2 NH_2$) (0.055 mmoles). The mixture was stirred at room temperature for 1.5 hours (compounds 25 and 26), 2 hours (compound 31) or 16 hours (compounds 27 to 30, 32 and 36). The reaction mixture was concentrated in vacuo and the residue purified by HPLC (gradient: 20% acetonitrile/80% water containing 0.1% trifluoroacetic acid to 80% acetonitrile/20% water at a rate of 1%/min) to afford the desired compound.

| Compound | $R^S$ | Yield (mg) | LC/MS $R_t$ (mins) System D | m/z (ES⁻) |
|---|---|---|---|---|
| 25 | 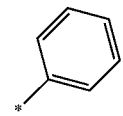 | 20 | 10.51 | 539 |
| 26 | 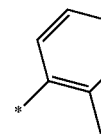 | 12 | 10.79 | 553 |
| 27 | 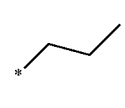 | 12.5 | 9.98 | 505 |
| 28 | 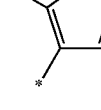 | 37.8 | 10.38 | 558 |
| 29 | 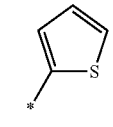 | 33 | 10.22 | 545 |
| 30 | 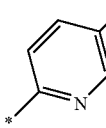 | 45 | 9.87 | 554 |
| 31 | 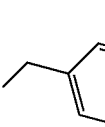 | 38 | 10.57 | 553 |

| Compound | R^S | Yield (mg) | LC/MS R$_t$ (mins) System D | m/z (ES$^-$) |
|---|---|---|---|---|
| 32 | | 42.8 | 10.78 | 607 |
| 36 | | 60 | 10.32 | 557 |
(f)  5-(4-Difluoromethoxy-phenyl)-2-methyl-furan-3-carboxylic acid {4-[2-(4-hydroxy-benzenesulfonylamino)-2-oxo-ethyl]-phenyl}-amide (35)
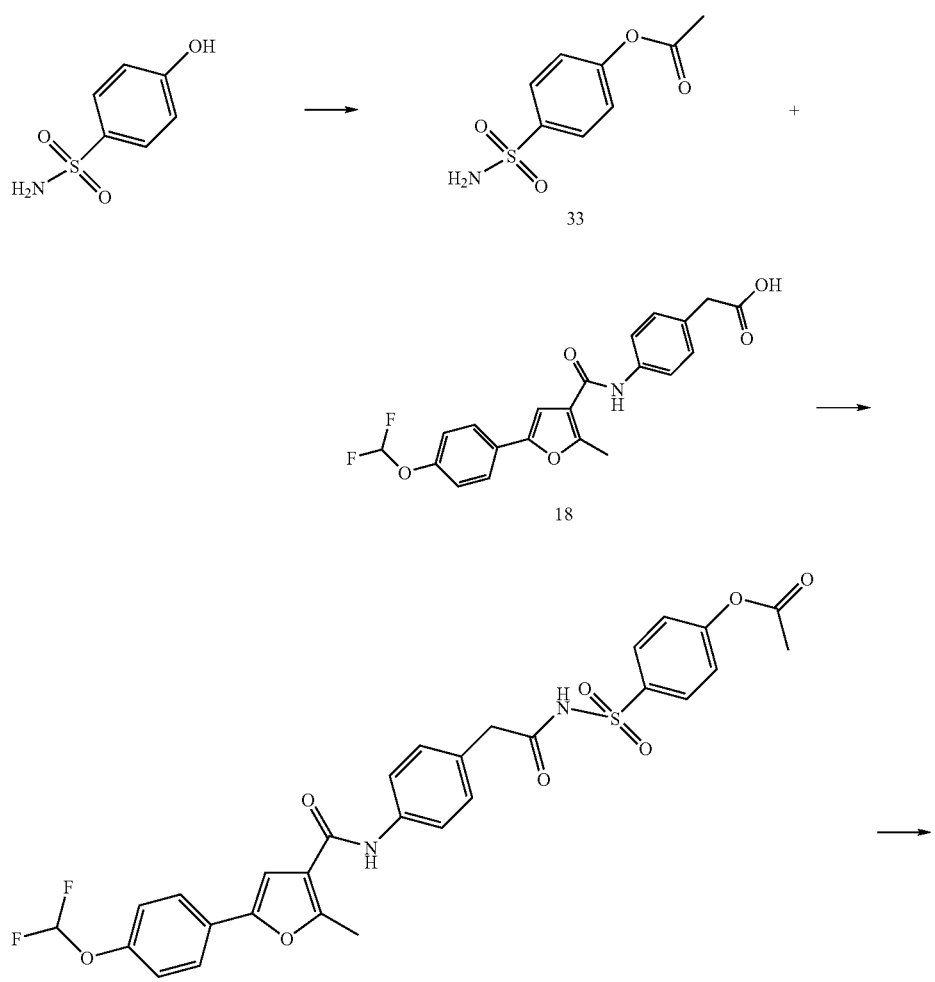

-continued

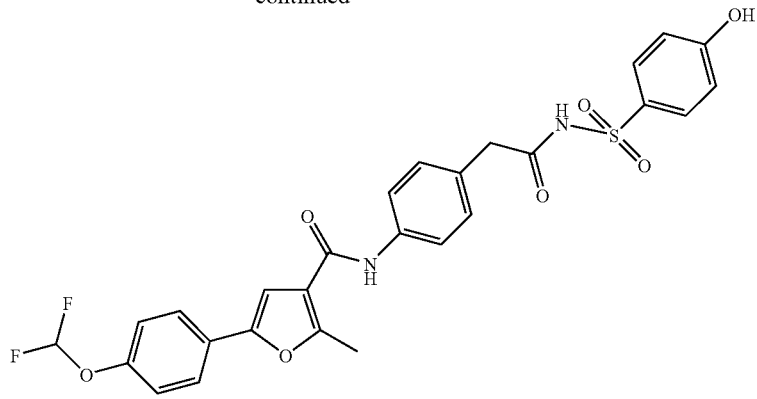

35

(i) A solution of sodium hydroxide (116 mg, 2.9 mmoles) in water (10 ml) was added to a stirred solution of 4-hydroxybenzenesulphonamide (500 mg, 2.9 mmoles) in water (30 ml). This mixture was treated with acetic anhydride (295 mg, 2.9 mmoles) and stirred at room temperature for 4.5 hours. The reaction mixture was filtered off and the resulting solid washed with water to afford acetic acid 4-sulphamoyl-phenyl ester (33)(348 mg) as a yellow solid. LC/MS System A; $R_t$ 2.06 mins.

(ii) In an analogous way to example 3(e), (4-{[5-(4-difluoromethoxy-phenyl)-2-methyl-furan-3-carbonyl]-amino}-phenyl)-acetic acid (18) (50 mg, 0.125 mmoles) was treated with acetic acid 4-sulphamoyl-phenyl ester (33)(29.2 mg, 0.137 mmoles). The mixture was stirred at room temperature for 16 hours. The reaction mixture was concentrated and the product (34) used as described in step (iii) without further purification. LC/MS System A; $R_t$ 3.89 mins, m/z (ES$^+$)=599 (M+H for $C_{29}H_{24}F_2N_2O_8S$).

(iii) Sodium methoxide (6.8 mg, 0.125 mmoles) and water (1 ml) were added to a stirred solution of acetic acid 4-[2-(4-{[5-(4-difluoromethoxy-phenyl)-2-methyl-furan-3-carbonyl]-amino}-phenyl)-acetylsulphamoyl]-phenyl ester (34) (74.5 mg, 0.125 mmoles) in methanol (10 ml). The reaction mixture was stirred at room temperature for 30 minutes, concentrated and the residue was purified by HPLC (gradient: 20% acetonitrile/80% water containing 0.1% trifluoroacetic acid to 80% acetonitrile/20% water at a rate of 1%/min) to afford compound (35)(18 mg) as a white solid. LC/MS System D; $R_t$=9.48 mins, m/z (ES$^-$)=555 (M–H for $C_{27}H_{22}F_2N_2O_7S$).

Example 4

Biological Results

Binding Ability to Human EP Receptors

Membranes were prepared from cells stably transfected with human EP receptor cDNA. In brief, cells were cultured to confluency, scraped from culture flasks, and centrifuged (800 g, 8 minutes, 4° C.). Cells were twice washed in ice cold homogenisation buffer containing 10 mMTris-HCl, 1 mM EDTA.2Na, 250 mM sucrose, 1 mM PMSF, 0.3 mM indomethacin, pH 7.4, homogenised and re-centrifuged as before. The supernatant was stored on ice and pellets re-homogenised and re-spun. Supernatants were pooled and centrifuged at 40000 g, 10 minutes, 4° C. Resultant membrane pellets were stored at –80° C. until use.

For assay, membranes expressing human $EP_4$, $EP_3$, $EP_2$ or $EP_1$ receptors were incubated in Millipore (MHVBN45) plates containing assay buffer, radiolabelled [$^3$H]PGE$_2$ and 0.1 to 10 000 nM concentrations of compounds. Incubations were performed at suitable temperatures and for suitable times to allow equilibrium to be reached. Non-specific binding was determined in the presence of 10 uM PGE$_2$. Bound and free radiolabel was separated by vacuum manifold filtration using appropriate wash buffers, and bound radiolabel was determined by scintillation counting. Constituents of each of the buffers are included in table 1 below.

The affinity or p$K_i$ of each compound for each receptor was calculated from the concentration causing 50% radioligand displacement (IC$_{50}$) using the Cheng-Prusoff equation:

$$Ki = \frac{IC_{50}}{1 + \left(\frac{\text{radioligand concentration}}{\text{radioligand } KD}\right)}$$

This approach follows that set out in Kenakin, T. P., Pharmacologic analysis of drug receptor interaction. Raven Press, New York, 2$^{nd}$ edition.

TABLE 1

| Receptor | $EP_1$ | $EP_2$ | $EP_3$ | $EP_4$ |
|---|---|---|---|---|
| Protein/well | 6.5 μg | 8 μg | 5 μg | 5 μg |
| Final [$^3$H-PGE$_2$] | 3.6 nM | 3 nM | 2.5 nM | 1 nM |
| Buffer Assay | 10 mM MES pH 6.0; 10 mM MgCl$_2$; 1 mM | 10 mM MES pH 6.0; 10 mM | 10 mM MES pH 6.0; 10 mM | 10 mM MES pH 6.0; 10 mM |

TABLE 1-continued

| Receptor Protein/well Final [$^3$H-PGE$_2$] | EP$_1$ 6.5 μg 3.6 nM | EP$_2$ 8 μg 3 nM | EP$_3$ 5 μg 2.5 nM | EP$_4$ 5 μg 1 nM |
|---|---|---|---|---|
| Wash | EDTA, 3 uM Indomethacin 10 mM MES pH 6.0; 10 mM MgCl$_2$ | MgCl$_2$; 1 mM EDTA 10 mM MES pH 6.0; 10 mM MgCl$_2$ | MgCl2; 1 mM EDTA, 100 uM GTP-gamma-S 10 mM MES pH 6.0; 10 mM MgCl$_2$ | MgCl$_2$; 1 mM EDTA, 3 uM Indomethacin 10 mM MES pH 6.0; 1 mM EDTA |

The results are presented as pK$_i$ values in table 2 below.

TABLE 2

| Compound | EP$_4$ | EP$_2$ | EP$_3$ |
|---|---|---|---|
| 4 | >5 | <5 | <5 |
| 6 | >6 | <5 | <5 |
| 10 | >6 | <5.5 | <5 |
| 13 | >6 | <5 | <5 |
| 18 | >6 | <5.5 | <5 |
| 20 | >5 | <5 | <5 |
| 21 | >7 | <6 | <5 |
| 22 | >6 | <6 | <5 |
| 23 | >7 | <6 | <5 |
| 24 | >6 | <7 | <5 |
| 25 | >7 | <6 | <5 |
| 26 | >7 | <6.5 | <5 |
| 27 | >6 | <5 | <5 |
| 28 | >6 | <5 | <5 |
| 29 | >7 | <5.5 | <5 |
| 30 | >7 | <6 | <5 |
| 31 | >7 | <6 | <5 |
| 32 | >7 | <5.5 | <5.5 |
| 35 | >7 | <5.5 | <5 |
| 36 | >7 | <6 | <5 |

The invention claimed is:

1. A compound of formula (I):

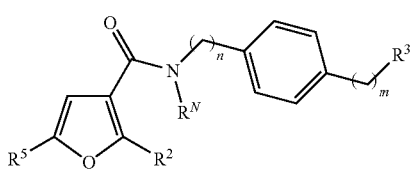

or a salt, hydrate or chemically protected form thereof, wherein:
either
R$^2$ is H or an optionally substituted C$_{1-4}$ alkyl group and R$^5$ is an optionally substituted C$_{5-7}$ aryl; or
R$^5$ is H or an optionally substituted C$_{1-4}$ alkyl group and R$^2$ is an optionally substituted C$_{5-7}$ aryl; m and n can be 0 or 1, and m+n=1 or 2
R$^N$ is H or optionally substituted C$_{1-4}$ alkyl
R$^3$ is either:
carboxy or tetrazole-5-yl
with the proviso that the compound in which R$^3$ is carboxy, n is 0, m is 1, R$^N$ is H, R$^2$ is methyl and R$^5$ is phenyl is excluded.

2. A compound according to claim 1, wherein R$^5$ is an optionally substituted C$_{5-7}$ aryl group and R$^2$ is H or the optionally substituted C$_{1-4}$ alkyl group.

3. A compound according to claim 2, wherein R$^2$ is selected from H or an optionally substituted C$_{1-3}$ alkyl group.

4. A compound according to claim 3, wherein R$^2$ is a methyl group.

5. A compound according to claim 2, wherein R$^5$ is a C$_6$ aryl group.

6. A compound according to claim 5, wherein R$^5$ is phenyl.

7. A compound according to claim 1 wherein the C$_{5-7}$ aryl group of R$^2$ and R$^5$ is substituted by substituents selected from C$_{1-7}$ alkoxy groups.

8. A compound according to claim 1, wherein n+m=1.

9. A compound according to claim 8, wherein n is 0 and m is 1.

10. A compound according to claim 1, wherein R$^N$ is H or methyl.

11. A method of treating a primary headache disorder comprising administering to a patient in need of treatment an effective amount of a compound according to claim 1 or a pharmaceutically acceptable salt thereof.

12. A pharmaceutical composition comprising a compound according to claim 1 or a pharmaceutically acceptable salt thereof together with a pharmaceutically acceptable carrier or diluent.

13. The method according to claim 11 wherein the primary headache disorder is a migraine.

* * * * *